US012691236B2

(12) United States Patent
Hunter et al.

(10) Patent No.: US 12,691,236 B2
(45) Date of Patent: Jul. 28, 2026

(54) ULTRASONIC BREATH ACTUATED RESPIRATORY DROPLET DELIVERY DEVICE AND METHODS OF USE

(71) Applicant: Pneuma Respiratory, Inc., Boone, NC (US)

(72) Inventors: Charles Eric Hunter, Boone, NC (US); John H. Hebrank, Boone, NC (US); Chengjie Li, Shenzhen City (CN); Judson Sidney Clements, Boone, NC (US)

(73) Assignee: PNEUMA RESPIRATORY, INC., Boone, NC (US)

( * ) Notice: Subject to any disclaimer, the term of this patent is extended or adjusted under 35 U.S.C. 154(b) by 1147 days.

(21) Appl. No.: 17/609,610

(22) PCT Filed: May 11, 2020

(86) PCT No.: PCT/US2020/032383
§ 371 (c)(1),
(2) Date: Nov. 8, 2021

(87) PCT Pub. No.: WO2020/227717
PCT Pub. Date: Nov. 12, 2020

(65) Prior Publication Data
US 2022/0226587 A1     Jul. 21, 2022

Related U.S. Application Data

(60) Provisional application No. 62/912,543, filed on Oct. 8, 2019, provisional application No. 62/883,030, filed
(Continued)

(51) Int. Cl.
*A61M 15/00*     (2006.01)
*A61M 15/06*     (2006.01)

(52) U.S. Cl.
CPC .... *A61M 15/0085* (2013.01); *A61M 15/0021* (2014.02); *A61M 15/06* (2013.01);
(Continued)

(58) Field of Classification Search
CPC ............ A61M 15/001; A61M 15/0085; A61M 15/0021; A61M 15/06; A61M 15/0003;
(Continued)

(56) References Cited

U.S. PATENT DOCUMENTS

| | | |
|---|---|---|
| 3,934,585 A | 1/1976 | Maurice |
| 3,970,250 A | 7/1976 | Drews |

(Continued)

FOREIGN PATENT DOCUMENTS

| | | |
|---|---|---|
| AU | 2012258488 | 1/2013 |
| CA | 2364248 | 8/2006 |

(Continued)

OTHER PUBLICATIONS

Copley, "Understanding cascade impaction and its importance for inhaler testing," Copley Scientific, Copley White Paper [serial online], Jul. 2007 [retrieved on May 7, 2017]. Retrieved from the Internet: URL: http://www.copleyscientific.com/files/ww/articles/Understanding%20Cascade%20Impaction%20White%20Paper.pdf; 6 pp.
(Continued)

*Primary Examiner* — Bradley H Philips
*Assistant Examiner* — Kira B Daher
(74) *Attorney, Agent, or Firm* — Polsinelli PC

(57) ABSTRACT

An ultrasonic droplet delivery device and related methods for delivering precise and repeatable amounts of a substance to a user for respiratory use is disclosed. The ultrasonic droplet delivery device generally comprises a body housing, a mouthpiece having an ejector mechanism, and a fluid cartridge having at least one fluid reservoir. In certain
(Continued)

embodiments, the ejector mechanism may comprise at least one ultrasonic actuator and at least one aperture plate with a plurality of openings formed through its thickness for ejecting droplets. The device may further comprise at least one differential pressure sensor configured to activate the ejector mechanism upon sensing a pre-determined pressure change within the device to thereby generate the ejected stream of droplets.

19 Claims, 14 Drawing Sheets

Related U.S. Application Data on Aug. 5, 2019, provisional application No. 62/871, 688, filed on Jul. 8, 2019, provisional application No. 62/851,910, filed on May 23, 2019, provisional application No. 62/845,664, filed on May 9, 2019.

(52) U.S. Cl.
CPC ................. *A61M 2205/123* (2013.01); *A61M 2205/3306* (2013.01); *A61M 2205/3331* (2013.01); *A61M 2205/3553* (2013.01); *A61M 2205/7536* (2013.01); *A61M 2205/8206* (2013.01); *A61M 2206/11* (2013.01)

(58) Field of Classification Search
CPC ........... A61M 15/0095; A61M 15/0035–0036; A61M 2205/123; A61M 2205/3306; A61M 2205/3331; A61M 2205/3553; A61M 2205/7536; A61M 2205/8206; A61M 2205/125; A61M 2205/27; A61M 2205/3561; A61M 2205/3592; A61M 2205/502; A61M 2205/505; A61M 2205/581; A61M 2205/583; A61M 2205/587; A61M 2205/6009; A61M 2205/6018; A61M 2205/6072; A61M 2206/11; A61M 11/005; A61M 2016/0039; A61M 2016/0018; A61M 2016/0027; A61M 2209/045; B05B 17/0684; B05B 17/0623; B05B 17/0676; A24F 40/10
See application file for complete search history.

(56) References Cited

U.S. PATENT DOCUMENTS

| | | | |
|---|---|---|---|
| 5,021,701 A | | 6/1991 | Takahashi et al. |
| 5,164,740 A | | 11/1992 | Ivri |
| 5,363,842 A | | 11/1994 | Mishelevich et al. |
| 5,435,282 A | * | 7/1995 | Haber ............... A61M 15/0065 |
| | | | 239/338 |
| 5,487,378 A | | 1/1996 | Robertson et al. |
| 5,586,550 A | | 12/1996 | Ivri et al. |
| 5,607,410 A | | 3/1997 | Branch |
| 5,630,793 A | | 5/1997 | Rowe |
| 5,694,919 A | * | 12/1997 | Rubsamen ........ A61M 15/0066 |
| | | | 128/200.14 |
| 5,758,637 A | | 6/1998 | Ivri et al. |
| 5,826,570 A | | 10/1998 | Goodman et al. |
| 5,828,394 A | | 10/1998 | Khuri-Yakub et al. |
| 5,881,716 A | | 3/1999 | Wirch et al. |
| 5,884,620 A | | 3/1999 | Gonda et al. |
| 5,894,841 A | | 4/1999 | Voges |
| 5,906,202 A | | 5/1999 | Schuster et al. |
| 5,938,117 A | * | 8/1999 | Ivri ......................... B41J 2/025 |
| | | | 239/4 |
| 6,011,062 A | | 1/2000 | Schneider et al. |
| 6,062,212 A | | 5/2000 | Davison et al. |
| 6,071,498 A | | 6/2000 | Narodylo et al. |
| 6,085,740 A | | 7/2000 | Ivri et al. |
| 6,196,219 B1 | | 3/2001 | Hess et al. |
| 6,235,177 B1 | | 5/2001 | Borland et al. |
| 6,443,146 B1 | * | 9/2002 | Voges ................ A61M 15/025 |
| | | | 128/200.14 |
| 6,615,826 B1 | | 9/2003 | Gabrio et al. |
| 6,637,430 B1 | | 10/2003 | Voges et al. |
| 6,896,910 B2 | | 5/2005 | Kim et al. |
| 6,978,941 B2 | | 12/2005 | Litherland et al. |
| 6,981,499 B2 | | 1/2006 | Anderson et al. |
| 7,191,777 B2 | | 3/2007 | Brand et al. |
| 7,198,044 B2 | | 4/2007 | Trueba |
| 7,219,664 B2 | | 5/2007 | Ruckdeschel et al. |
| 7,628,339 B2 | | 12/2009 | Ivri et al. |
| 7,648,957 B2 | | 1/2010 | Heyden et al. |
| 7,708,011 B2 | | 5/2010 | Hochrainer et al. |
| 7,883,031 B2 | | 2/2011 | Collins, Jr. et al. |
| 7,900,625 B2 | | 3/2011 | Kleinstreuer et al. |
| 7,954,486 B2 | * | 6/2011 | Papania ............. A61M 11/005 |
| | | | 128/200.14 |
| 7,976,140 B2 | | 7/2011 | Umeda |
| 8,012,136 B2 | | 9/2011 | Collins, Jr. et al. |
| 8,367,734 B1 | | 2/2013 | Gao et al. |
| 8,474,452 B2 | | 7/2013 | Gumaste et al. |
| 8,545,463 B2 | | 10/2013 | Collins, Jr. et al. |
| 8,555,874 B2 | | 10/2013 | Fink et al. |
| 8,684,980 B2 | | 4/2014 | Hunter et al. |
| 8,733,935 B2 | | 5/2014 | Ballou, Jr. et al. |
| 8,753,308 B2 | | 6/2014 | Palmer et al. |
| 8,936,021 B2 | | 1/2015 | Collins, Jr. |
| 8,985,100 B2 | | 3/2015 | Minocchieri et al. |
| 9,087,145 B2 | | 7/2015 | Ballou, Jr. et al. |
| 9,227,029 B2 | | 1/2016 | Addington et al. |
| 9,242,054 B2 | | 1/2016 | Fink et al. |
| 9,352,108 B1 | * | 5/2016 | Reed ................ A61M 15/0091 |
| 9,452,274 B2 | | 9/2016 | Addington et al. |
| 9,463,486 B2 | | 10/2016 | Wilkerson et al. |
| 9,539,604 B2 | | 1/2017 | Wilkerson et al. |
| 9,956,360 B2 | | 5/2018 | Germinario et al. |
| 9,962,507 B2 | | 5/2018 | Germinario et al. |
| 10,449,314 B2 | | 10/2019 | Germinario et al. |
| 10,525,220 B2 | | 1/2020 | Hunter et al. |
| 10,568,543 B2 | | 2/2020 | Yan |
| 10,898,666 B2 | | 1/2021 | Germinario et al. |
| 2002/0002975 A1 | | 1/2002 | Power |
| 2002/0032387 A1 | | 3/2002 | Geva et al. |
| 2002/0046750 A1 | | 4/2002 | Gonda et al. |
| 2002/0071871 A1 | | 6/2002 | Snyder et al. |
| 2002/0121274 A1 | | 9/2002 | Borland et al. |
| 2003/0072717 A1 | | 4/2003 | Reinhold et al. |
| 2003/0101991 A1 | | 6/2003 | Trueba |
| 2003/0127538 A1 | * | 7/2003 | Patel ................ A61M 15/0068 |
| | | | 239/338 |
| 2003/0140921 A1 | | 7/2003 | Smith et al. |
| 2003/0150445 A1 | | 8/2003 | Power et al. |
| 2003/0196654 A1 | | 10/2003 | Stein |
| 2003/0205229 A1 | | 11/2003 | Crockford et al. |
| 2004/0009231 A1 | | 1/2004 | Jackson et al. |
| 2004/0139963 A1 | | 7/2004 | Ivri et al. |
| 2004/0195403 A1 | | 10/2004 | Atterybury et al. |
| 2004/0215157 A1 | | 10/2004 | Peclat et al. |
| 2004/0256487 A1 | | 12/2004 | Collins, Jr. et al. |
| 2005/0011514 A1 | | 1/2005 | Power et al. |
| 2005/0077315 A1 | | 4/2005 | Pavlu et al. |
| 2005/0121025 A1 | | 6/2005 | Gamard et al. |
| 2005/0150489 A1 | | 7/2005 | Dunfield et al. |
| 2005/0172476 A1 | | 8/2005 | Stone et al. |
| 2005/0172958 A1 | | 8/2005 | Singer et al. |
| 2005/0217666 A1 | | 10/2005 | Fink et al. |
| 2005/0224075 A1 | | 10/2005 | Childers et al. |
| 2005/0236501 A1 | | 10/2005 | Zimlich, Jr. et al. |
| 2007/0023036 A1 | | 2/2007 | Grychowski et al. |
| 2007/0044793 A1 | | 3/2007 | Kleinstreuer et al. |
| 2007/0083677 A1 | | 4/2007 | Cecka et al. |
| 2007/0119969 A1 | | 5/2007 | Collins, Jr. et al. |
| 2007/0125370 A1 | | 6/2007 | Denyer et al. |
| 2007/0157931 A1 | | 7/2007 | Parker et al. |
| 2007/0240714 A1 | | 10/2007 | Dunne et al. |

(56)　　　　　References Cited

U.S. PATENT DOCUMENTS

| | | |
|---|---|---|
| 2007/0248645 A1 | 10/2007 | Bague et al. |
| 2007/0267010 A1 | 11/2007 | Fink et al. |
| 2008/0000470 A1 | 1/2008 | Minocchieri et al. |
| 2008/0059228 A1 | 3/2008 | Bossi et al. |
| 2008/0142010 A1 | 6/2008 | Weaver et al. |
| 2008/0243050 A1 | 10/2008 | Power et al. |
| 2008/0271732 A1 | 11/2008 | Weaver et al. |
| 2008/0283057 A1 | 11/2008 | Rohrschneider et al. |
| 2008/0295827 A1 | 12/2008 | Kobayashi |
| 2008/0308096 A1 | 12/2008 | Borgschulte et al. |
| 2009/0038610 A1 | 2/2009 | Bogh et al. |
| 2009/0093772 A1 | 4/2009 | Genosar et al. |
| 2009/0107492 A1 | 4/2009 | Ooida |
| 2009/0114218 A1 | 5/2009 | Veatch |
| 2009/0114742 A1 | 5/2009 | Collins, Jr. |
| 2009/0118243 A1 | 5/2009 | Gjorstrup |
| 2009/0134235 A1 | 5/2009 | Ivri |
| 2009/0167812 A1 | 7/2009 | Asai et al. |
| 2009/0192443 A1 | 7/2009 | Collins, Jr. |
| 2009/0212133 A1 | 8/2009 | Collins, Jr. |
| 2009/0235925 A1 | 9/2009 | Power et al. |
| 2009/0270752 A1 | 10/2009 | Coifman |
| 2009/0272818 A1 | 11/2009 | Valpey, III et al. |
| 2009/0314292 A1 | 12/2009 | Overfield et al. |
| 2009/0317496 A1 | 12/2009 | Park et al. |
| 2010/0037894 A1 | 2/2010 | Rouse et al. |
| 2010/0078013 A1 | 4/2010 | Power et al. |
| 2010/0089395 A1 | 4/2010 | Power et al. |
| 2010/0156995 A1 | 6/2010 | Kanda et al. |
| 2010/0222752 A1 | 9/2010 | Collins, Jr. et al. |
| 2010/0282247 A1 | 11/2010 | Kadrichu et al. |
| 2011/0036346 A1 * | 2/2011 | Cohen .................... A24F 40/60 |
| | | 128/200.14 |
| 2011/0108025 A1 | 5/2011 | Fink et al. |
| 2011/0230820 A1 | 9/2011 | Lillis et al. |
| 2011/0253805 A1 | 10/2011 | Lee |
| 2011/0277761 A1 * | 11/2011 | Terry ................ A61M 15/0001 |
| | | 128/203.12 |
| 2012/0037154 A1 | 2/2012 | Gallem et al. |
| 2012/0048265 A1 | 3/2012 | Smaldone |
| 2012/0266878 A1 | 10/2012 | Watanabe et al. |
| 2012/0291781 A1 | 11/2012 | Kaufmann et al. |
| 2013/0079732 A1 | 3/2013 | Burt et al. |
| 2013/0150812 A1 | 6/2013 | Hunter et al. |
| 2013/0172830 A1 | 7/2013 | Hunter et al. |
| 2013/0239956 A1 | 9/2013 | Schulz et al. |
| 2013/0267864 A1 | 10/2013 | Addington et al. |
| 2013/0269694 A1 | 10/2013 | Patton et al. |
| 2013/0284165 A1 | 10/2013 | Krimsky |
| 2013/0299607 A1 | 11/2013 | Wilkerson et al. |
| 2013/0327323 A1 | 12/2013 | Rubin |
| 2013/0330400 A1 | 12/2013 | Perkins et al. |
| 2013/0334335 A1 | 12/2013 | Wilkerson et al. |
| 2013/0334339 A1 | 12/2013 | Xu |
| 2014/0037735 A1 | 2/2014 | Montgomery |
| 2014/0116426 A1 * | 5/2014 | Mullinger ............. A61M 15/00 |
| | | 128/200.14 |
| 2014/0187969 A1 | 7/2014 | Hunter et al. |
| 2014/0190496 A1 | 7/2014 | Wensley et al. |
| 2014/0213925 A1 | 7/2014 | Chan et al. |
| 2014/0336618 A1 | 11/2014 | Wilkerson et al. |
| 2015/0018694 A1 | 1/2015 | Gomo |
| 2015/0101596 A1 | 4/2015 | Hogan |
| 2015/0136155 A1 | 5/2015 | Verleur et al. |
| 2015/0164375 A1 | 6/2015 | Schindhelm et al. |
| 2015/0174348 A1 | 6/2015 | Tunnell et al. |
| 2015/0196060 A1 | 7/2015 | Wensley et al. |
| 2015/0328151 A1 | 11/2015 | Ballou, Jr. et al. |
| 2015/0352301 A1 | 12/2015 | Stedman et al. |
| 2016/0001018 A1 | 1/2016 | Fink et al. |
| 2016/0001019 A1 | 1/2016 | Fink et al. |
| 2016/0106341 A1 | 4/2016 | Adam et al. |
| 2016/0245830 A1 | 8/2016 | Mace et al. |
| 2016/0310982 A1 | 10/2016 | Von Hollen |
| 2016/0325055 A1 | 11/2016 | Cameron |

| | | |
|---|---|---|
| 2016/0354557 A1 | 12/2016 | McPherson Allnutt et al. |
| 2017/0035924 A1 | 2/2017 | Yang et al. |
| 2017/0039344 A1 | 2/2017 | Bitran et al. |
| 2017/0106153 A1 | 4/2017 | Davidson et al. |
| 2017/0106155 A1 | 4/2017 | Reed et al. |
| 2017/0158776 A1 | 6/2017 | Feltquate et al. |
| 2017/0203058 A1 | 7/2017 | Davidson et al. |
| 2017/0203323 A1 | 7/2017 | Gschwind et al. |
| 2017/0224706 A1 | 8/2017 | Surber |
| 2017/0274163 A1 | 9/2017 | Oliveras et al. |
| 2017/0291000 A1 * | 10/2017 | Salegui Echeveste ...................... |
| | | B65D 83/14 |
| 2017/0304565 A1 | 10/2017 | Allosery |
| 2017/0304566 A1 | 10/2017 | Allosery |
| 2017/0319796 A1 | 11/2017 | Germinario et al. |
| 2017/0319797 A1 * | 11/2017 | Germinario ....... A61M 15/0003 |
| 2017/0333646 A1 | 11/2017 | Hemy et al. |
| 2018/0056018 A1 | 3/2018 | Canvin et al. |
| 2018/0116871 A1 | 5/2018 | Hunter et al. |
| 2018/0193175 A1 | 7/2018 | Bluecher et al. |
| 2018/0317557 A1 | 11/2018 | Monsees et al. |
| 2018/0344955 A1 | 12/2018 | Germinario et al. |
| 2018/0369515 A1 | 12/2018 | Germinario et al. |
| 2019/0117907 A1 | 4/2019 | Germinario et al. |
| 2019/0125985 A1 | 5/2019 | Germinario et al. |
| 2019/0125986 A1 | 5/2019 | Germinario et al. |
| 2019/0125987 A1 | 5/2019 | Germinario et al. |
| 2019/0134330 A1 | 5/2019 | Germinario et al. |
| 2019/0166913 A1 * | 6/2019 | Trzecieski ............ A61M 15/06 |
| 2019/0358420 A1 | 11/2019 | Hunter et al. |
| 2020/0276398 A1 | 9/2020 | Hebrank et al. |
| 2020/0289770 A1 | 9/2020 | Hebrank et al. |
| 2020/0353186 A1 | 11/2020 | Hebrank et al. |
| 2021/0106772 A1 | 4/2021 | Hebrank et al. |
| 2021/0236745 A1 | 8/2021 | Germinario et al. |
| 2021/0275760 A1 | 9/2021 | Hunter et al. |
| 2022/0001122 A1 | 1/2022 | Hunter et al. |

FOREIGN PATENT DOCUMENTS

| | | | |
|---|---|---|---|
| CN | 1788806 | 6/2006 | |
| CN | 104511072 | 4/2015 | |
| CN | 204995458 | 1/2016 | |
| CN | 205019058 | 2/2016 | |
| EP | 2724741 | 4/2014 | |
| JP | 2003-265994 | 9/2003 | |
| JP | 2006-68508 | 3/2006 | |
| JP | 2013507152 A | 3/2013 | |
| KR | 10-2019-122453 | 10/2019 | |
| WO | WO 96/09846 | 4/1996 | |
| WO | WO 96/14163 | 5/1996 | |
| WO | WO 98/48873 | 11/1998 | |
| WO | WO 00/47335 | 8/2000 | |
| WO | WO 01/87378 | 11/2001 | |
| WO | WO 03/020349 | 3/2003 | |
| WO | WO 03/059413 | 7/2003 | |
| WO | WO 2004/078025 | 9/2004 | |
| WO | WO 2006/013952 | 2/2006 | |
| WO | WO 2006/083014 | 8/2006 | |
| WO | WO-2007024812 A1 * | 3/2007 | ........ A61M 16/0833 |
| WO | WO 2008/056986 | 5/2008 | |
| WO | WO 2008/058941 | 5/2008 | |
| WO | WO 2008/116165 | 9/2008 | |
| WO | WO 2009/012371 | 1/2009 | |
| WO | WO 2009/111612 | 9/2009 | |
| WO | 2011042212 A1 | 4/2011 | |
| WO | WO 2013/098334 | 7/2013 | |
| WO | WO 2013/158352 | 10/2013 | |
| WO | WO 2013/158967 | 10/2013 | |
| WO | WO 2013/173321 | 11/2013 | |
| WO | WO 2015/136529 | 9/2015 | |
| WO | WO 2016/001924 | 1/2016 | |
| WO | WO 2016/003738 | 1/2016 | |
| WO | WO 2017/056103 | 4/2017 | |
| WO | WO 2018/213834 | 11/2018 | |
| WO | WO 2019/071008 | 4/2019 | |
| WO | WO 2019/079461 | 4/2019 | |
| WO | WO 2019/219865 | 11/2019 | |

(56)             References Cited

FOREIGN PATENT DOCUMENTS

| WO | WO 2020/072478 | 4/2020 |
| WO | WO 2020/154497 | 7/2020 |
| WO | WO 2020/264501 | 12/2020 |

OTHER PUBLICATIONS

Kharitonov, "Exhaled markers of inflammatory lung diseases: ready for routine monitoring?" *Swiss Med Wkly*, 2004; 134: 175-192.

Broeders et al., "Inhalation Profiles in Asthmatics and COPD Patients: Reproducibility and Effect of Instruction," *Journal of Aerosol Medicine*, vol. 16, No. 2, 2003, 131-141.

Taube et al., "Use of a portable device to record maximum inspiratory flow in relation to dyspnoea in patients with COPD," *Respiratory Medicine*, 2011, 105, 316-312.

Canadian Office Action issued Nov. 6, 2023 in corresponding Canadian Application No. 3,139,686.

Japanese Office Action issued Nov. 20, 2023 in corresponding Japanese Application No. 2021-565880.

* cited by examiner

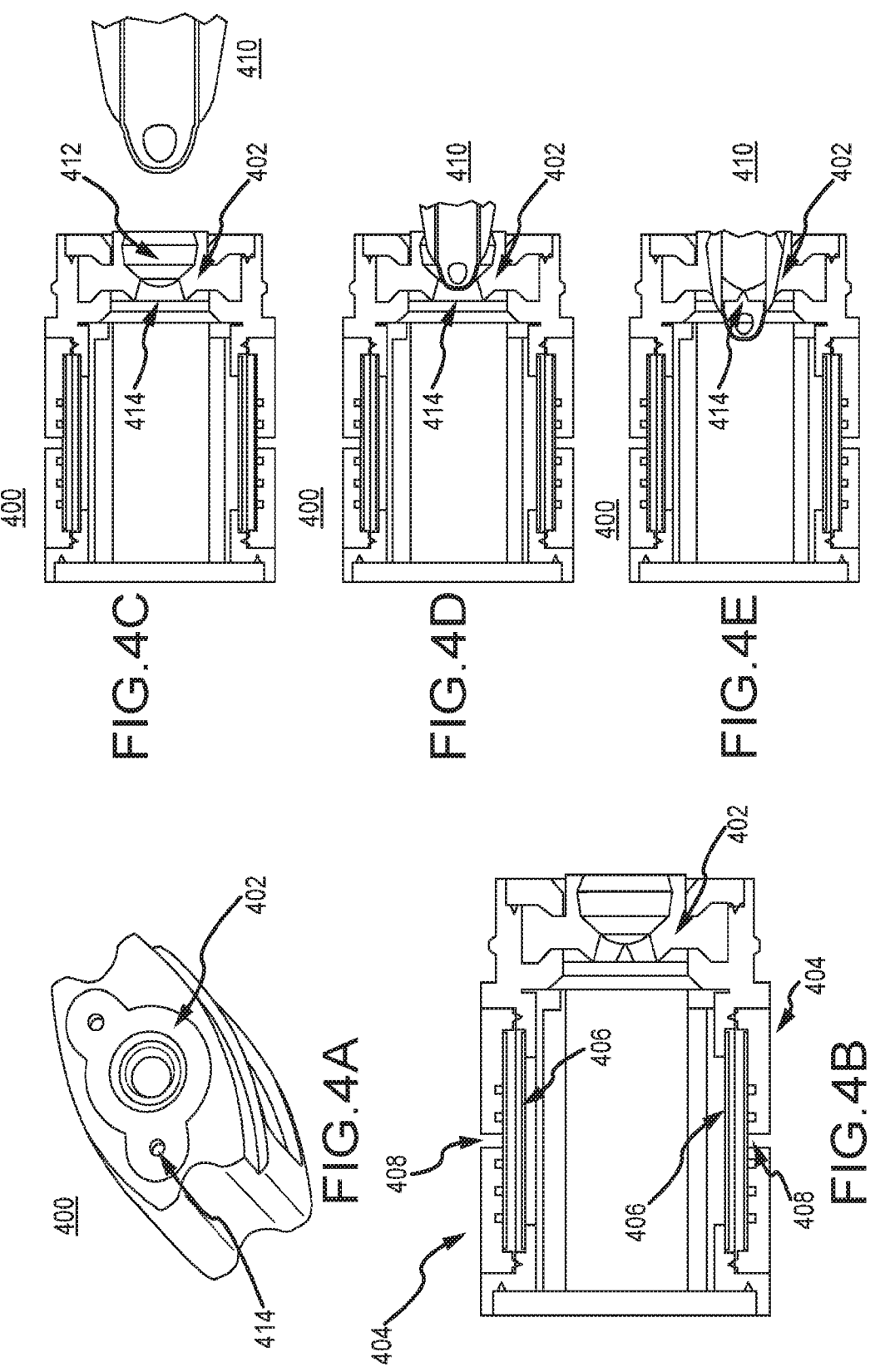

502

504

500

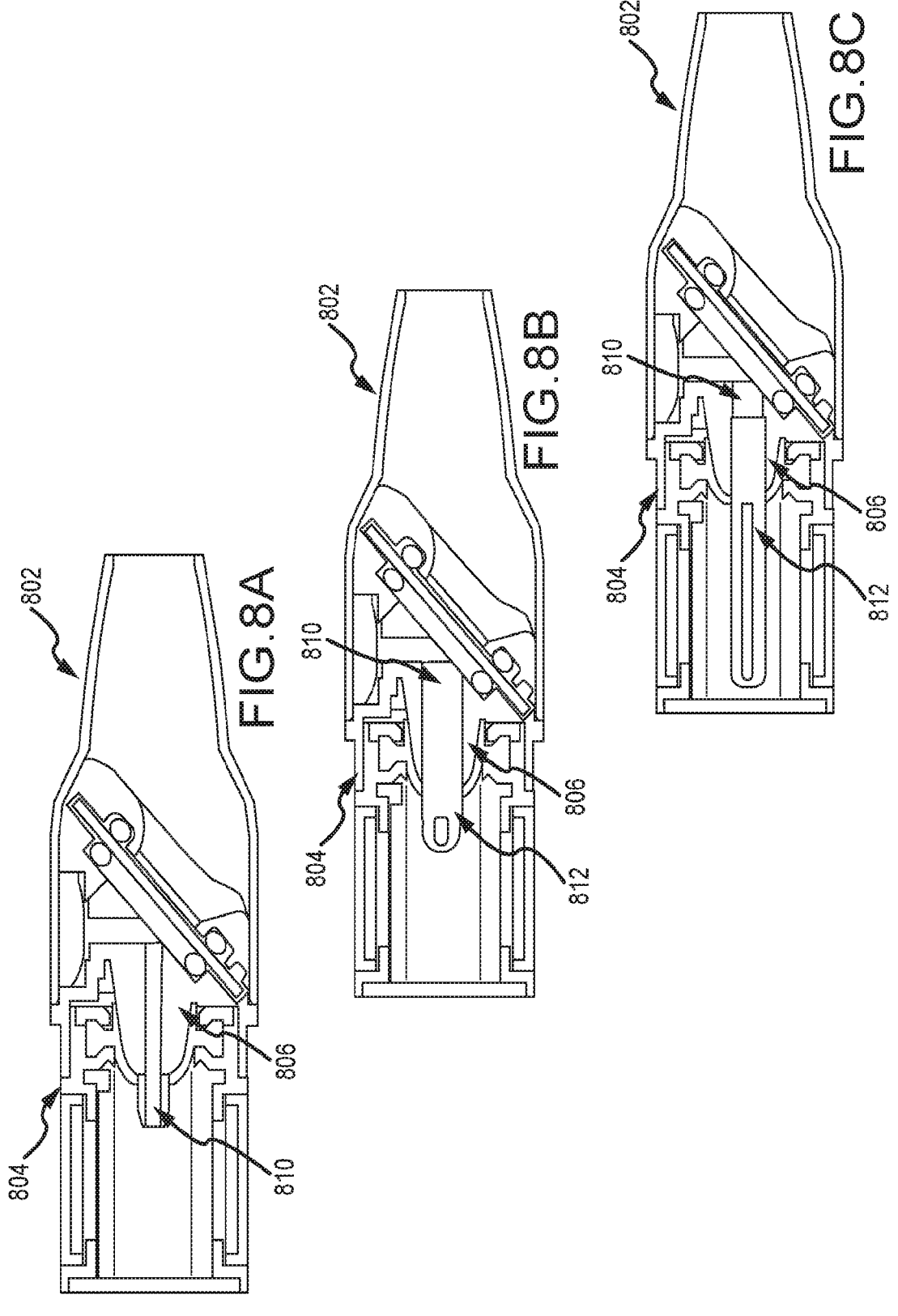

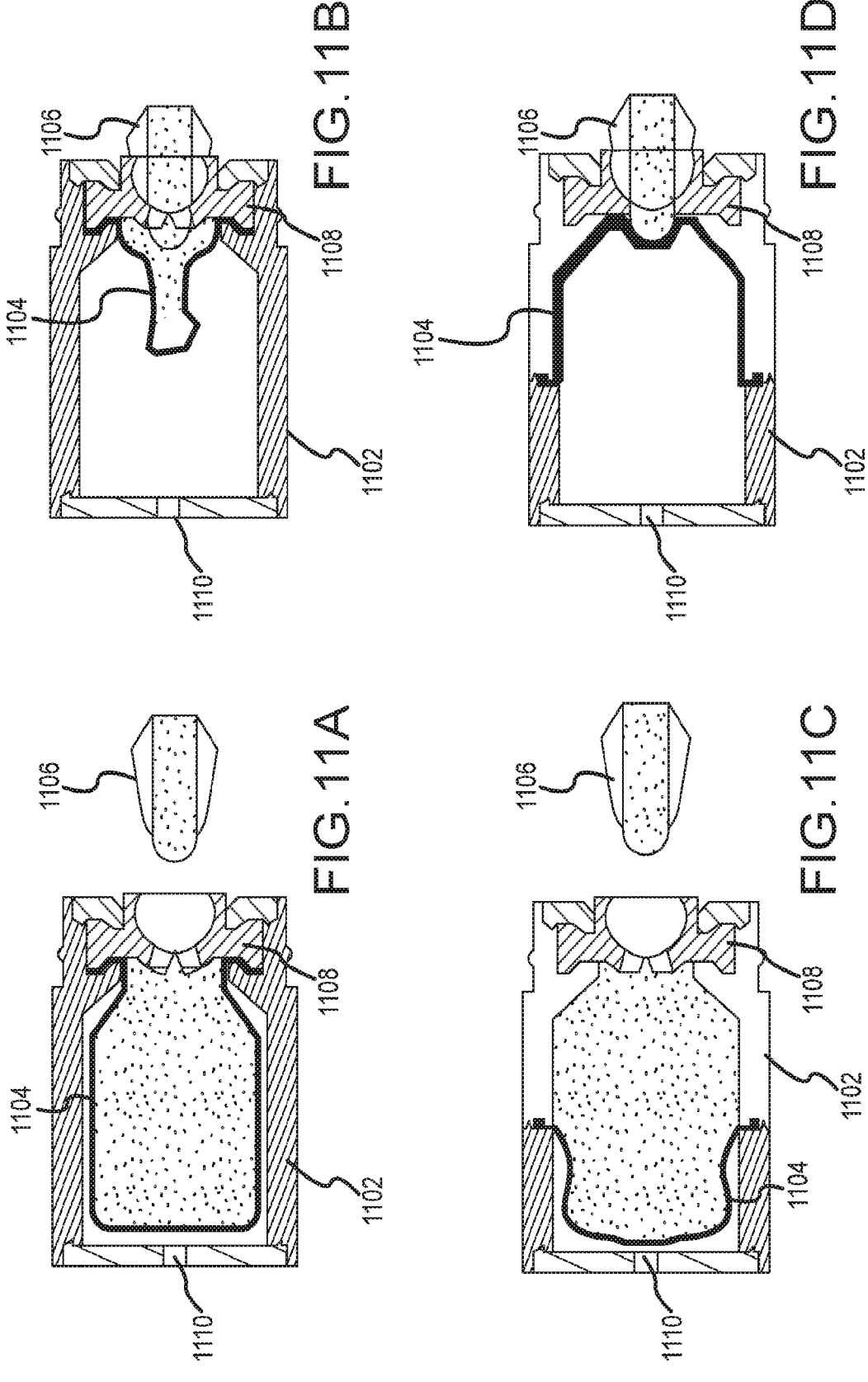

ULTRASONIC BREATH ACTUATED RESPIRATORY DROPLET DELIVERY DEVICE AND METHODS OF USE

CROSS-REFERENCE TO RELATED APPLICATIONS

This application is a U.S. national phase application under 35 U.S.C. § 371 of International Application No. PCT/US2020/032383, filed on May 11, 2020 entitled "ULTRASONIC BREATH ACTUATED RESPIRATORY DROPLET DELIVERY DEVICE AND METHODS OF USE," which claims priority under 35 U.S.C. § 119(e) to U.S. Patent Application No. 62/845,664, filed May 9, 2019 entitled "ULTRASONIC BREATH ACTUATED PULMONARY DROPLET DELIVERY DEVICE AND METHODS OF USE," U.S. Patent Application No. 62/851,910, filed May 23, 2019 entitled "ULTRASONIC BREATH ACTUATED PULMONARY DROPLET DELIVERY DEVICE AND METHODS OF USE," U.S. Patent Application No. 62/871,688, filed Jul. 8, 2019 entitled "ULTRASONIC BREATH ACTUATED PULMONARY DROPLET DELIVERY DEVICE AND METHODS OF USE," U.S. Patent Application No. 62/883,030, filed Aug. 5, 2019 entitled "ULTRASONIC BREATH ACTUATED PULMONARY DROPLET DELIVERY DEVICE AND METHODS OF USE," and U.S. Patent Application No. 62/912,543, filed Oct. 8, 2019 entitled "ULTRASONIC BREATH ACTUATED RESPIRATORY DROPLET DELIVERY DEVICE AND METHODS OF USE," the entire contents of which are incorporated herein by reference in their entireties for all purposes.

FIELD OF THE INVENTION

This disclosure relates to respiratory droplet delivery devices, and more specifically to droplet delivery devices for the delivery of fluids to the respiratory system.

BACKGROUND OF THE INVENTION

The use of droplet generating devices for the delivery of substances to the lungs is an area of large interest. A major challenge is providing a device that delivers an accurate, consistent, and verifiable amount of substance, with a droplet size that is suitable for successful delivery of substance to the targeted area of the respiratory system.

Aerosol verification, delivery and inhalation of the correct amount at the desired times is important. A need exists to insure that users correctly use droplet generating devices, and that they administer the proper amount at desired time. Problems emerge when users misuse or incorrectly delivery substances to the respiratory system.

Currently most inhaler type systems such as metered dose inhalers (MDI) and pressurized metered dose inhalers (p-MDI) or pneumatic and ultrasonic-driven devices generally produce droplets with high velocities and a wide range of droplet sizes including large droplet that have high momentum and kinetic energy. Droplets and aerosols with such high momentum do not reach the distal lung or lower pulmonary passageways, but rather are deposited in the mouth and throat. As a result, larger total drug doses are required to achieve the desired deposition in targeted respiratory areas. These large doses increase the probability of unwanted side effects.

Aerosol plumes generated from current droplet delivery systems, as a result of their high ejection velocities and the rapid expansion of the substance carrying propellant, may lead to localized cooling and subsequent condensation, deposition and crystallization of substance onto the device surfaces. Blockage of device surfaces by deposited substance residue is also problematic.

Accordingly, there is a need for a droplet delivery device that delivers droplets of a suitable size range, avoids surface fluid deposition and blockage of apertures, with an amount that is verifiable, and provides feedback regarding correct and consistent usage of the device to users.

SUMMARY OF THE INVENTION

In one aspect of the disclosure, an ultrasonic droplet delivery device for delivering a fluid as an ejected stream of droplets to the respiratory system of a subject. The device generally comprises a mouthpiece, a fluid cartridge, a body housing, and at least one differential pressure sensor. In certain embodiments, the mouthpiece is positioned at an airflow exit of the device, the mouthpiece comprising one or more air flow entrance ports, an airflow exit opening, an electronically actuated ejector mechanism, an ejection chamber, and a fluid transport mating extension. The fluid cartridge generally comprises at least one reservoir for receiving a volume of fluid, and at least one sealing mechanism, the fluid cartridge disposed within or in fluid communication with the mouthpiece. The body housing comprises a power source and control board. The at least one differential pressure sensor is positioned within the mouthpiece or positioned within the body housing and in fluid communication with the mouthpiece, the at least one differential pressure sensor configured to activate the ejector mechanism upon sensing a pre-determined pressure change within the mouthpiece to thereby generate the ejected stream of droplets.

In certain embodiments, the electronically actuated ejector mechanism is in fluid communication with the reservoir at a fluid cartridge side of the ejector mechanism, and configured to generate the ejected stream of droplets, the ejector mechanism comprising a piezoelectric actuator and an aperture plate, the aperture plate having a plurality of openings formed through its thickness and the piezoelectric actuator operable to oscillate the aperture plate at a frequency to thereby generate the ejected stream of droplets; and the ejection chamber is located adjacent the ejector mechanism on the fluid cartridge side of the ejector mechanism.

In certain embodiments, the fluid transport mating extension is positioned within the mouthpiece at a fluid cartridge side of the mouthpiece. The fluid transport mating extension is configured to provide for a fluid path between the fluid cartridge and the ejector mechanism. The fluid transport mating extension may interface with or extend through the sealing mechanism of the fluid cartridge to create fluid communication between the fluid cartridge and the ejector mechanism.

In certain embodiments, the one or more air flow entrance ports of the mouthpiece are configured as an air inlet flow element, wherein the air inlet flow element and mouthpiece are configured to facilitate non-turbulent airflow across an exit side of the aperture plate and to provide sufficient airflow through the mouthpiece during use.

In other aspects, a method for delivering an agent as an ejected stream of droplets in a respirable range to the pulmonary system of a user is provided. In certain embodiments, the method comprises (a) generating an ejected stream of droplets via a ultrasonic droplet delivery device of the disclosure, wherein at least portion (e.g., at least about 50%) of the ejected stream of droplets have an average ejected droplet diameter of less than about 6 μm; and (b) delivering the ejected stream of droplets to the pulmonary system of the subject such that at least a portion (e.g., at least about 50%) of the mass of the ejected stream of droplets is delivered in a respirable range to the pulmonary system of a subject during use.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed descriptions are to be regarded as illustrative in nature and not restrictive.

DESCRIPTION OF THE DRAWINGS

FIG. 1A illustrates an embodiment wherein the ejector mechanism comprises a piezoelectric actuator and an ultrasonic horn. FIG. 1B illustrates an embodiment wherein the ejector mechanism is generally perpendicular to the direction of air flow through the device. FIG. 1C illustrates and embodiment wherein the ejector mechanism is orientated at an angle with reference to the direction of air flow through the device.

FIG. 2A shows the mouthpiece, fluid cartridge and body housing as separate elements. FIG. 2B shows the fluid cartridge interfaced with the mouthpiece to form a combined mouthpiece/fluid cartridge, with the body housing as a separate element. FIG. 2C shows the device fully assembled, with the mouthpiece/fluid cartridge secured to the body housing.

FIG. 3A shows a fluid cartridge facing side of an exemplary stopper, while FIG. 3B shows the ejector mechanism facing side of the exemplary stopper. FIG. 3C, FIG. 3D, and FIG. 3E illustrate various embodiments of a wheel spoke opening configuration, each having differing internal sealing structures. FIG. 3F shows a single cut opening configuration, FIG. 3G shows a cross cut opening configuration, and FIG. 3H shows a wheel spoke opening configuration.

FIG. 4A shows a perspective view of a self-sealing stopper secured to a fluid cartridge, in accordance with an embodiment of the disclosure. FIG. 4B shows a cross section of the fluid cartridge with self-sealing stopper of FIG. 4A. FIG. 4C, FIG. 4D, and FIG. 4E illustrate a fluid transport mating extension inserting into the fluid cartridge with self-sealing stopper of FIG. 4A.

FIG. 7A and FIG. 7B illustrate a capillary flow tube configured as a solid rod having external capillary flow channels. FIG. 7C illustrates a capillary flow tube configured as a hollow tube having internal capillary flow channels. FIG. 7D and FIG. 7E illustrate a capillary flow tube configured as a combined solid rod and hollow tube.

FIG. 8A, FIG. 8B and FIG. 8C illustrate alternative configurations of a combined mouthpiece/fluid cartridge, having different fluid transport mating extension configurations, in accordance with embodiments of the disclosure.

FIG. 9A shows the mouthpiece having a fluid transport mating extension including a wicking material, and a fluid cartridge as separate elements. FIG. 9B shows the combined mouthpiece/fluid cartridge of FIG. 9A. FIG. 9C shows the mouthpiece having a fluid transport mating extension including a capillary flow tube, and a fluid cartridge as separate elements. FIG. 9D shows the combined mouthpiece/fluid cartridge of FIG. 9C.

FIG. 10A shows the mouthpiece having a fluid transport mating extension including a wicking material, and a fluid cartridge as separate elements. FIG. 10B shows the combined mouthpiece/fluid cartridge of FIG. 10A.

FIGS. 11A-11D illustrate cross-sections of a various configurations of a fluid cartridge having a collapsible fluid reservoir. FIG. 11A shows a collapsible fluid reservoir secured to the fluid cartridge at the self-sealing stopper. FIG. 11B shows the fluid reservoir of FIG. 11A in a collapsed configuration. FIG. 11C shows a collapsible fluid reservoir secured to the fluid cartridge along the length of the fluid cartridge. FIG. 11D shows the fluid reservoir of FIG. 11C in a collapsed configuration.

Figures 1A, 1B, 1C:
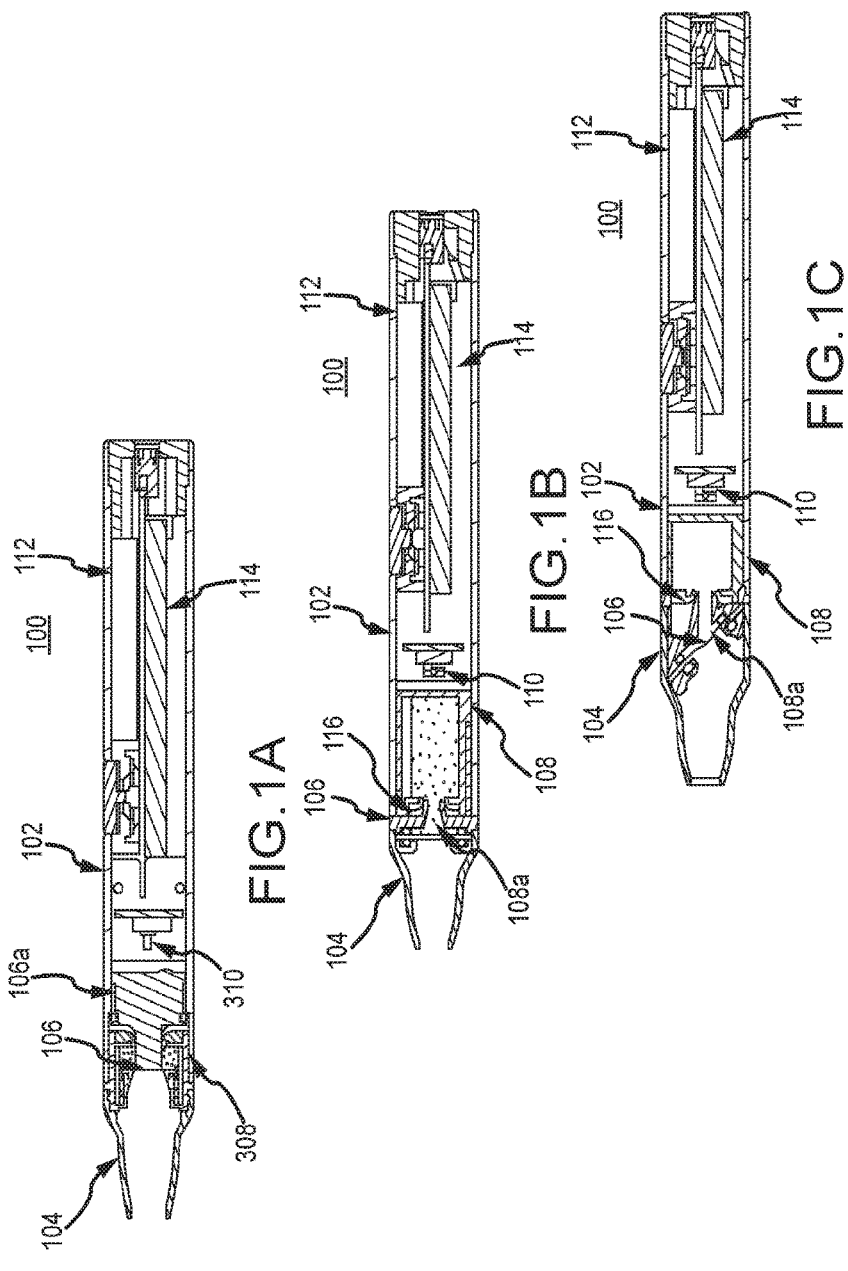
FIGS. 1A-1C illustrate cross-sections of various droplet delivery devices, according to certain embodiments of the disclosure.

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

DETAILED DESCRIPTION

Effective and efficient delivery of substances using respiratory droplet delivery devices to the desired areas of the respiratory system, and the synchronization of the administration of droplets with the inspiration/expiration cycle using such devices has always posed a problem. For instance, optimum deposition in alveolar airways generally requires droplets with aerodynamic diameters in the ranges of 1 to 6

μm, with droplets below about 4 μm shown to more effectively reach the alveolar region of the lungs and larger droplets above about 6 μm shown to typically deposited on the tongue or strike the throat and coat the bronchial passages. Smaller droplets, for example less than about 1 μm, penetrate more deeply into the lungs and have a tendency to be exhaled. As such, design of droplet delivery devices for respiratory use requires the ability to precisely target droplet sizes for a particular use.

Certain aspects of the disclosure relate to a breath actuated platform for delivery of inhaled substances, described herein as a respiratory droplet delivery device. The device provides substantial improvements over current inhaled delivery systems by improving precision, reliability, and delivery to a user. In certain embodiments, the device of the disclosure includes fully integrated monitoring capabilities designed to enhance user experience and compliance. In certain aspects, the ultrasonic droplet delivery devices described herein are useful for delivery of a fluid as an ejected stream of droplets to the respiratory system of a user and related methods of delivering safe, suitable, and repeatable dosages to the respiratory system of a user.

In certain aspects, the disclosure relates to an ultrasonic droplet delivery device for administering fluids to the respiratory system of a user with precise droplet size. In certain embodiments, the device comprises a body housing, a mouthpiece having an ejector mechanism, a fluid cartridge having at least one fluid reservoir. In certain embodiments, the ejector mechanism may comprise at least one ultrasonic actuator and at least one aperture plate with a plurality of openings formed through its thickness for ejecting droplets. The device may further comprise at least one differential pressure sensor configured to activate the ejector mechanism upon sensing a pre-determined pressure change within the device to thereby generate the ejected stream of droplets.

In certain embodiments, the droplet delivery device generally comprises a mouthpiece, a fluid cartridge, a body housing, and at least one differential pressure sensor. In certain embodiments, the mouthpiece is positioned at an airflow exit of the device, the mouthpiece comprising one or more air flow entrance ports, an airflow exit opening, an electronically actuated ejector mechanism, an ejection chamber, and a fluid transport mating extension. The fluid cartridge generally comprises at least one reservoir for receiving a volume of fluid, and at least one sealing mechanism, the fluid cartridge disposed within or in fluid communication with the mouthpiece. The body housing comprises a power source and control board. The at least one differential pressure sensor is positioned within the mouthpiece or positioned within the body housing and in fluid communication with the mouthpiece, the at least one differential pressure sensor configured to activate the ejector mechanism upon sensing a pre-determined pressure change within the mouthpiece to thereby generate the ejected stream of droplets.

In certain embodiments, the electronically actuated ejector mechanism is in fluid communication with the reservoir at a fluid cartridge side of the ejector mechanism, and configured to generate the ejected stream of droplets, the ejector mechanism comprising a piezoelectric actuator and an aperture plate, the aperture plate having a plurality of openings formed through its thickness and the piezoelectric actuator operable to oscillate the aperture plate at a frequency to thereby generate the ejected stream of droplets; and the ejection chamber is located adjacent the ejector mechanism on the fluid cartridge side of the ejector mechanism.

In certain embodiments, the fluid transport mating extension is positioned within the mouthpiece at a fluid cartridge side of the mouthpiece. The fluid transport mating extension is configured to provide for a fluid path between the fluid cartridge and the ejector mechanism. The fluid transport mating extension may interface with or extend through the sealing mechanism of the fluid cartridge to create fluid communication between the fluid cartridge and the ejector mechanism.

In certain embodiments, the one or more air flow entrance ports of the mouthpiece are configured as an air inlet flow element, wherein the air inlet flow element and mouthpiece are configured to facilitate non-turbulent airflow across an exit side of the aperture plate and to provide sufficient airflow through the mouthpiece during use.

In other aspects, the ultrasonic droplet delivery devices described herein are capable of delivering a defined volume of fluid in the form of an ejected stream of droplets such that an adequate and repeatable high percentage of the droplets are delivered into the desired location within the airways, e.g., the alveolar airways of a user during use. For instance, in certain embodiments, the stream of droplets may have an average ejected droplet diameter of less than about 6 microns, less than about 5 microns, less than about 4 microns, less than about 3 microns, less than about 2.6 microns, less than about 2.3 microns, less than about 2 microns, less than about 1.6 microns, less than about 1.3 microns, less than about 1 micron, etc.

In specific embodiments, the ejector mechanism is electronically breath activated by at least one differential pressure sensor located within the ultrasonic droplet delivery device upon sensing a pre-determined pressure change within the mouthpiece. In certain embodiments, such a pre-determined pressure change may be sensed during an inspiration cycle by a user of the device. In certain embodiments, the pressure sensor may be located in the mouthpiece, on the airflow exit side of the ejector mechanism. In other embodiments, the pressure sensor may be located in the body housing, and may be in fluid communication with the airflow exit side of the ejector mechanism.

In some aspects, the droplet delivery device further includes one or more air inlet flow elements positioned in the airflow at the airflow entrance of the device and configured to facilitate non-turbulent (i.e., laminar and/or transitional) airflow across the exit side of at least one aperture plate and to provide sufficient airflow to ensure that the ejected stream of droplets flows through the droplet delivery device during use. In some embodiments, the air inlet flow element may be positioned within the mouthpiece. In certain embodiments, the air inlet flow element(s) may be positioned behind the exit side of the aperture plate along the direction of airflow, or in-line or in front of the exit side of the aperture plate along the direction of airflow. In certain embodiments, the air inlet flow element(s) comprises one or more openings configured to increase or decrease internal pressure resistance within the droplet delivery device during use. For instance, in certain embodiments, the air inlet flow element (s) comprise an array of one or openings. In other embodiments, the air inlet flow element(s) comprise one or more baffles, e.g., wherein the one or more baffles comprise one or more airflow openings.

The airflow exit of the mouthpiece of the droplet delivery device through which the ejected aerosol of droplets exit as they are inhaled into a subject's airways, may be configured and have, without limitation, a cross sectional shape of a circle, oval, rectangular, hexagonal or other shape, while the shape of the length of the tube, again without limitation, may be straight, curved or have a Venturi-type shape.

In accordance with certain aspects of the disclosure, droplet delivery devices are disclosed which include at least one ultrasonic ejector mechanism in fluid communication with at least one aperture plate having a plurality of openings there through. In certain embodiments, the ultrasonic ejector mechanism may comprise a piezoelectric actuator, optionally amplified by an elongated ultrasonic "horn". Such ultrasonic "horn" actuators are an impedance matching device that are wide at a vibration generating, piezoelectric end and thin at a fluid contact, horn end.

In certain embodiments, exemplary ultrasonic horn actuators may be about half a wavelength long, and are typically made of metal, e.g., titanium, stainless steel or aluminum. The horn may be specially tapered, fluted, or a stepped rod, and produces displacements large enough to create a stream of droplets or aerosol. The horn is designed to allow for efficient coupling of piezo energy into fluid (i.e., small, high-stiffness motion to large, less-still motion). By way of non-limiting example, if the piezo's 1% strain creates a 1% strain in the horn, the horn being ten times longer potentially has ten times the displacement.

In certain embodiments, if configured to include an ultrasonic horn, the aperture plate may be positioned close to the fluid end of the horn, but not specifically touching the horn, as will be described in further detail herein. The horn may generally be long enough that it and the piezo element form a half wavelength structure with a nodal point having a point of high stress and minimal motion between the midpoint of the body of the horn and the step in the horn. Horn lengths may be optimized during design, with parameters set due based on their multiple masses. By way of non-limiting example, titanium horns may be used in high temperature, high abrasion settings to address high nodal stress.

Without intending to be limited by theory, a horn extracts energy from a vibrating piezo element, and transmits it into fluid to be ejected through the aperture plate. In practice, the horn may be stretch in resonance to magnify the amplitude of the piezo element vibration. Accordingly, the horn material should preferably stretch with low loss and sufficient strength at the nodal point to support the stress associated with the stretch (strain). In certain aspects, horn length is minimally half a wavelength, e.g., at 100 kHz. By way of example, polymer horns would generally need to be twice as long because the speed of sound is about half for polymers as compared to metals.

Exemplary droplet delivery devices 100 of the disclosure are illustrated in FIGS. 1A-1C, with a mouthpiece 104, ejector mechanism 106, fluid cartridge 108, pressure/flow sensor 110, control board 112, power source/battery 114, and a body housing 102. The ejector mechanism 106 may be interfaced with or located within the mouthpiece 304 or the fluid cartridge 108.

As explained in further detail herein, the ejector mechanism may be orientated at various angles within the device, with respect to the direction of droplet generation, airflow through the device, and internal surfaces within the device. Without intending to be limited by theory, it is believed that orientation of the ejector mechanism with respect to the direction of droplet generation, airflow through the device, and internal surface within the device serves to optimize droplet size distribution via inertial filtering, which filters and excludes larger droplets from the droplet plume.

In some embodiments, the ejector mechanism may be oriented perpendicularly (e.g., vertical) to the direction of airflow through the device, such that droplets are initially ejected into the direction of airflow. Such a configuration minimizes inertial filtering of generated droplets, allowing most droplets to flow in the entrained airflow within the mouthpiece (other than impacts of droplets at the sidewalls of the mouthpiece and inertial settling along the air flow path). In other embodiments, the ejector mechanism may be orientated at an angle with respect to the direction of airflow through the device. By way of example, the ejector mechanism may be oriented at about 5° from perpendicular, about 10° from perpendicular, about 15° from perpendicular, about 20° from perpendicular, about 25° from perpendicular, about 30° from perpendicular, about 35° from perpendicular, about 40° from perpendicular, about 45° from perpendicular, etc. In such embodiments, the droplets may be ejected into the airflow at an angle, such that smaller droplets are able to flow in the entrained airflow within the mouthpiece, and larger droplets are more likely to impact the sidewalls of the mouthpiece along the air flow path (or settle out along the air flow path).

FIG. 1A illustrates an embodiment wherein the ejector mechanism 106 includes an acoustic horn 106a. During use, droplets are ejected from the fluid reservoir through the openings in the aperture plate of the ejector mechanism when the ultrasonic actuator vibrates. The ultrasonic actuator vibrates when a piezoelectric actuator affixed to or interfaced with an ultrasonic horn and operable to oscillate the horn is activated by a control circuit located on the electronics board. The horn amplifies the amplitude of the piezo vibration into the fluid within the fluid reservoir. In other embodiments (not shown), the fluid cartridge may interface with an aperture plate on one side and a thin ultrasonic port on the opposite side. The ultrasonic port may be any material suitable to conduct the vibrational energy, e.g., a thin or elastic film. The ultrasonic horn/piezo actuator may then transmit vibrational energy to the fluid cartridge through the ultrasonic port.

In certain embodiments, for effective coupling of ultrasonic vibration (energy transfer) between the end of the horn and the fluid, the end of the horn must transmit both compression and tension phases of each cycle of ultrasonic vibration into the fluid. As described herein, the horn does not need to physically couple to or touch the aperture plate to achieve ejection of droplets. Rather, the horn needs to be in vibrational communication with the aperture plate so as to allow energy transfer between the horn and the aperture plate, e.g., within about 0.1 to 2 mm from the aperture plate. In certain embodiments, this may be accomplished by both the aperture plate and horn being supported on structures which attach to the outer shell of the body of the device. However, the present disclosure contemplates further configurations for achieving effective and efficient coupling.

In accordance with certain aspects, the devices of the disclosure address challenges of fluid leakage or evaporation at the interface between the fluid cartridge and the ultrasonic horn. For example, fluid within the fluid reservoir may be inhibited from leaking by an O-ring seal between the horn and the reservoir. In an alternative embodiment for inhibiting fluid leakage at the horn connection, the horn may be connected to a floating "wall" or ultrasonic port of the cartridge that communicates the vibration to the aperture plate by an internal element. This wall or port can be a compliant material such as an elastic rubber or a plastic sheet that flexes. In certain embodiments, the total area of the wall that moves may be minimized to avoid ultrasonic energy loss. The spacing between the wall and the aperture plate also may also be minimized (millimeter or fraction of a millimeter) to accommodate desired fluid reservoir sizing.

The connection between the horn and wall may be configured to transmit both compressive and tensile forces of the ultrasonic vibration. In certain embodiment, the connection may be accomplished by suitable mechanical connection, such as a set screw or "bayonet" connection where the horn has tangs which insert into groves in a transfer element that is part of the cartridge and a twist allows the tangs to be held rigidly for axial motion. The internal element that transmits the vibration is part of the attachment membrane and is short to have minimal effect on the vibration characteristics of the horn. In yet an additional embodiment for inhibiting fluid leakage at the horn connection, the ultrasonic horn may be connected to the fluid reservoir via a rigid connection block to transmit both the tensile and compressive aspects of the ultrasonic vibration. This embodiment is particularly suitable for configuration where the fluid volume is small (typically, example a single dose cartridge). Again a set screw or bayonet type of connection may be used to connect the horn to the rigid connection block.

FIG. 1B illustrates an embodiment wherein the ejector mechanism is aligned in an orientation generally perpendicular (e.g., vertical) to the direct of air flow through the device. As illustrated in the embodiment of FIG. 1B, a fluid ejection chamber 108a is located behind the ejector mechanism 106, and a sealing mechanism 116 is located between the ejector mechanism 106 and the fluid cartridge 108. A configuration wherein the ejector mechanism is oriented vertically can allow the stream of ejected droplets to flow in the air flow through the device in a generally unimpeded manner, i.e., there is minimal inertial filtering of droplets due to impact along the sides of mouthpiece.

FIG. 1C illustrates an embodiment wherein the ejector mechanism is aligned in an orientation that is angled to the direction of air flow through the device. Again, in this embodiment, a fluid ejection chamber 108a is located behind the ejector mechanism, and a sealing mechanism 116 is located between the ejector mechanism 106 and the fluid cartridge 108. A configuration wherein the ejector mechanism is oriented at an angle can allow the stream of ejected droplets to flow in the air flow through the device in a manner so as to be subject to inertial filtering due to impact along the sides of the mouthpiece. This inertial filtering can serve to capture and remove larger droplets from the air flow stream to the extent desired.

In certain embodiments, the mouthpiece may be interfaced with (and optionally removable and/or replaceable), integrated into, or part of the body housing. In other embodiments, the mouthpiece may be interfaced with (and optionally removable and/or replaceable), integrated into, or part of the fluid cartridge.

Figures 2A, 2B, 2C:
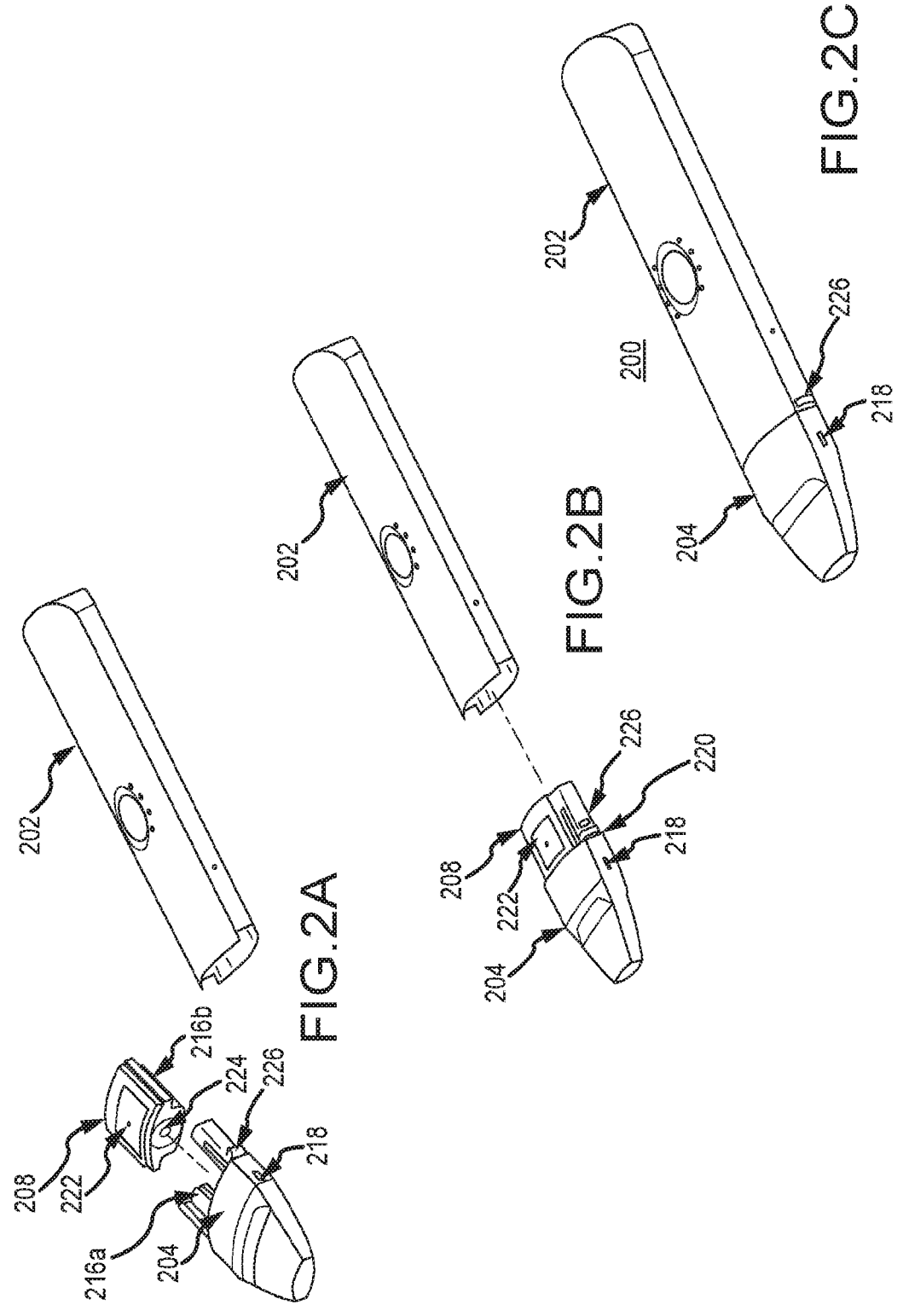
FIGS. 2A-2C illustrate perspective views of a droplet delivery device in accordance with embodiments of the disclosure.

With reference to FIGS. 2A-2C, in certain aspects, the body housing 202 and mouthpiece 204 may fit together to enclose the fluid cartridge 208 and the ejector mechanism (not shown) within an enclosed device 200. As illustrated in FIG. 2A, in certain embodiments, the mouthpiece 204, fluid cartridge 208, and body housing 202 may each be configured as separate elements. With reference to FIG. 2B, the mouthpiece 204 may house the ejector mechanism (not shown), and the fluid cartridge 208 may first be connected to the mouthpiece 204 to place the fluid cartridge 208 in fluid communication with the ejector mechanism (not shown) within the mouthpiece 204. As shown in FIG. 2C, once the fluid cartridge 208 is connected to the mouthpiece 204, the combined mouthpiece/fluid cartridge 220 may be inserted into the body housing 202 to enclose the fluid cartridge 208 within the device 200.

In certain embodiments, body housing 202 may comprise a power source (e.g., batteries) and electronics (e.g., a control board) for controlling operation and actuation of the ejector mechanism, flow/pressure sensors, etc. The mouthpiece 204 may include cartridge slides 216a, and the fluid cartridge 208 may include cartridge rails 216b configured to cooperate with the cartridge slides 216a to thereby secure the fluid cartridge 208 to the mouthpiece 204. The fluid cartridge 408 may include one or more housing locks 226 configured to interface with and lock into the body housing 202. The fluid cartridge 208 may also include one or more vents 222, and may include an access port 224 that may be configured so as to be self-sealing.

The mouthpiece 204 is generally located at an airflow exit of the device 200, and one or more airflow entrance ports 218 are generally located on airflow entrances of the mouthpiece 204 or body housing 202 (not shown). The ejector mechanism may be located within the device 200, e.g., within the mouthpiece 204 or fluid cartridge 208, so as to be in fluid communication with the fluid cartridge such that the ejector mechanism can receive fluid from the fluid reservoir during use. In certain embodiments, the ultrasonic (e.g., piezoelectric) actuator is interfaced with the aperture plate and operable to oscillate the aperture plate at a frequency to thereby generate an ejected stream of droplets. As illustrated, the fluid cartridge 208 may be removable from the device 200 and replaceable. The fluid cartridge may include one or more fluid reservoir(s) that enclose a single or multiple administrations of a composition to be delivered to a user.

The droplet delivery devices of the disclosure may include one or more sealing mechanisms. In certain embodiments, devices of the disclosure are configured to minimize evaporation from multi-use cartridges or single-use cartridges that are placed in the device after removing sealing tape from the fluid cartridge. By way of example, in one embodiment, the mouthpiece may include one or more sealing mechanisms to cover any fluid exit paths when not in use and/or to cover the aperture plate when not in use. For example, in one embodiment, a face seal may be provided which covers the aperture plate when not in use. Any suitable face seal may be used, for instance, a seal may be part of a mouthpiece cap that is closed by the user after an inhalation. The cap may include a spring loaded face seal that presses against a smooth stainless steel surface within the mouthpiece but outside the aperture plate. In another embodiment, a seal may be provided between the connection of the piezo horn and the fluid cartridge.

In other embodiments, the fluid cartridge and/or mouthpiece may include one or more sealing mechanisms at the interface of the fluid cartridge and the ejector mechanism to minimize evaporation of the fluid within the reservoir. In some embodiments, the fluid cartridge may have a removable sealing tape which prevents evaporation prior to attachment to the body. In other embodiments, the device may include one or more sealing mechanisms to minimize evaporation at the connection point between the fluid cartridge and body.

Figures 3A, 3B, 3C, 3D, 3E, 3F, 3G, 3H:
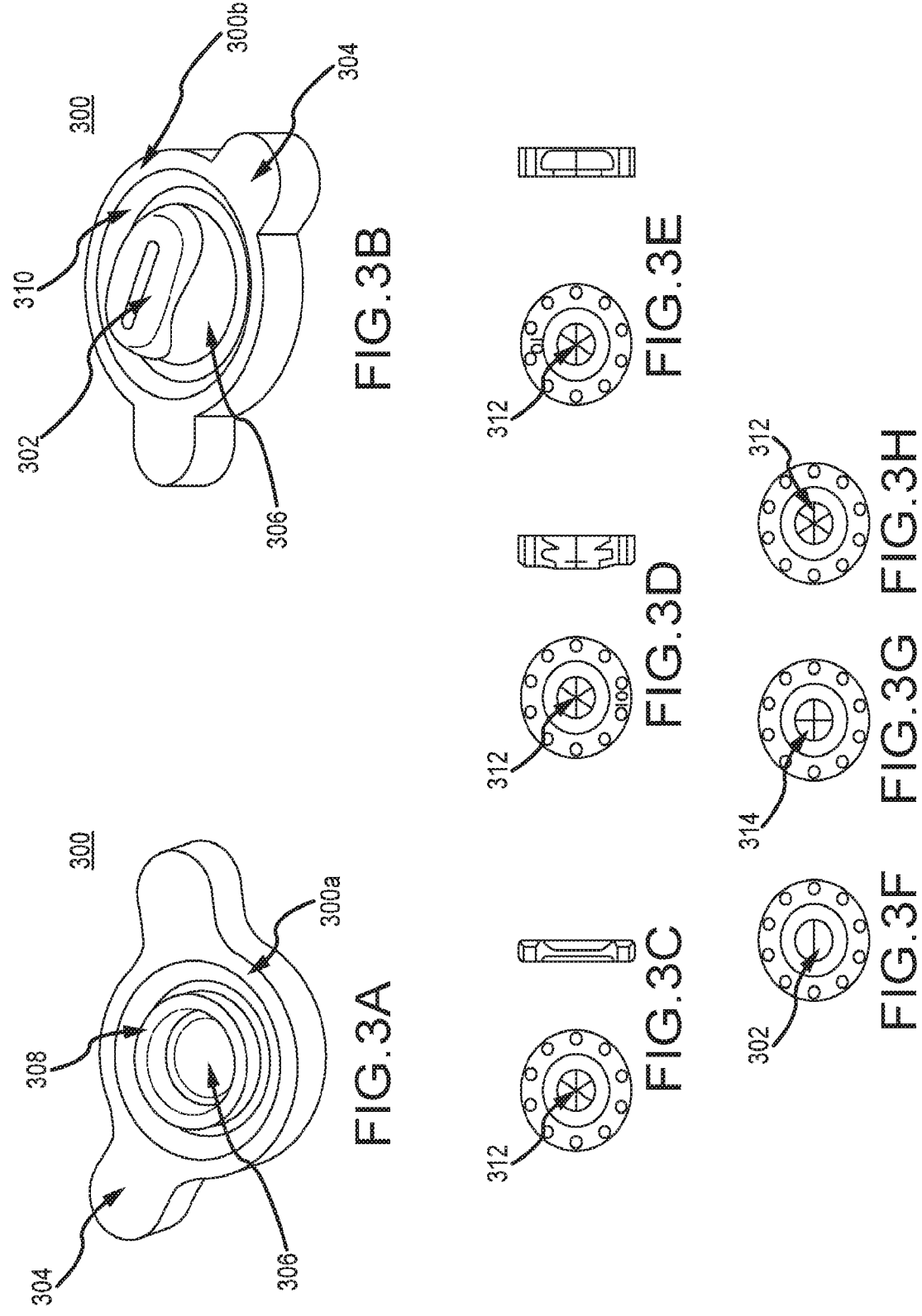
FIGS. 3A-3H illustrate various embodiments of a self-sealing stopper, in accordance with aspects of the disclosure.

By way of non-limiting example, the sealing mechanism at the interface between the fluid cartridge and the ejector mechanism may include a self-sealing polymer (e.g., rubber) type stopper. With reference to FIGS. 3A-3B, an exemplary self-sealing stopper 300 is illustrated, including a single cut configuration 302. FIG. 3A illustrates the ejector mechanism facing side of the stopper 300a, while FIG. 3B illustrates the fluid cartridge facing side of the stopper 300b. In certain embodiments, the stopper may include one or more additional access ports 304, e.g., to facilitate filling or sampling access to the fluid reservoir. For instance, one port may be used for filling of the fluid reservoir (e.g., high throughput automated filling), and the other port may be used to provide venting of air during the filling process. Once filled, the ports may be sealed by any suitable means, e.g., via a plug closure, polymer sealant, etc.

In certain embodiments, the sealing mechanism may be located on the fluid cartridge at the interface to the ejector mechanism. The mouthpiece and/or the ejector mechanism may include a fluid transport mating extension (e.g., a protrusion or needle like extension) to provide for a fluid path between the fluid cartridge and the ejector mechanism. The mating extension may interface with or extend through the sealing mechanism to create fluid communication between the fluid cartridge and the ejector mechanism. The stopper may be shaped to as to be generally planar on both sides (FIGS. 3C-3H), or may be shaped to facilitate placement of the mating extension of the mouthpiece or ejector mechanism (FIGS. 3A-3B). For instance, as shown in FIGS. 3A-3B, the stopper may include a central domed structure 306 shaped to facilitate placement of the mating extension, with a generally concave surface on ejector mechanism facing side of the stopper 300a, and a generally convex protrusion on the fluid cartridge facing side of the stopper 300b. One or more surfaces of the central domed structure 306 may include sealing rings 308 and troughs 310 to facilitate sealing of the stopper during use.

Alternative opening cut configurations of the self-sealing stopper are illustrated in FIGS. 3C-3F. FIGS. 3C-3E illustrate a spoke wheel cut configuration 312 with alternative internal sealing configurations designed to optimize cooperation with mating extensions of the mouthpiece. FIGS. 3F-3H illustrate alternative cut configurations, including without limitation a single cut configuration 302 (FIG. 3F), a cross cut configuration 314 (FIG. 3G), and a spoke wheel configuration 312 (FIG. 3H). However, the disclosure is not limited to the illustrated cut configuration, and any suitable configuration may be used.

FIG. 4A illustrates a self-sealing stopper 402 interfaced with a fluid cartridge 400, and FIG. 4B illustrates a cross-sectional view of an exemplary fluid cartridge 400 interfaced with a self-sealing stopper 402. In certain embodiments, the stopper may include one or more additional access ports 414, e.g., to facilitate filling or sampling access to the fluid reservoir. For instance, one port may be used for filling of the fluid reservoir (e.g., high throughput automated filling), and the other port may be used to provide venting of air during the filling process. Once filled, the ports may be sealed by any suitable means, e.g., via a plug closure, polymer sealant, etc.

As illustrated in FIG. 4B, the fluid cartridge 400 may include one or more vents 404. In certain embodiments, the vents 404 may include an internal super hydrophobic filter or surface treated mesh 406 on the fluid facing side, and an external opening 408. The external opening 408 may be configured to include a spiral vent airflow path, or may be configured to include one or more holes. In certain embodiments, the internal filter/mesh may be formed from a polymer (e.g., polytetrafluoroethylene (PTFE)) or metal mesh with openings formed therethrough to provide for venting. The mesh may be surface treated so as to have a desired surface contact angle (e.g., so as to be hydrophilic or hydrophobic, depending on its intended use). Generally, if the surface contact angle for water is smaller than 90°, the surface is considered hydrophilic and if the surface contact angle for water is larger than 90°, the surface is considered hydrophobic. In certain embodiments, the mesh may be surface treated to as to achieve a high contact angle (i.e., hydrophobic), or to achieve a low contact angle (i.e., hydrophilic). By way of non-limiting example, the mesh may be surface treated, e.g., via micromolding, chemical etching, dry etching (e.g., with ionized oxygen or plasma), etc.

FIGS. 4C-4E show an exemplary embodiment wherein a mating extension 410 is positioned in-line with the stopper 402 (FIG. 4C), the mating extension 410 is then inserted into the central domed structure 412 of the stopper 402 (FIG. 4D), and finally, the mating extension 410 punches through the self-sealing opening 414 of the stopper 402 to form a fluid path between the fluid cartridge 400 and the ejector mechanism (not shown) (FIG. 4E).

The mating extension may be configured in any suitable manner so as to provide a fluid flow path between the fluid cartridge and the ejector mechanism when in use. By way of example, with reference to FIG. 5, the mating extension 502 may be integral with the mouthpiece 500. In certain embodiments, the mating extension 502 may be positioned at a fluid cartridge facing side of the mouthpiece, and may be generally adjacent the ejector mechanism (not shown). The mating extension may include any suitable fluid flow path or configuration to provide a fluid flow path between the fluid cartridge and the ejector mechanism when is use. For instance, suitable wicking materials, capillary fins, and/or flow channels may be used.

Figure 5:
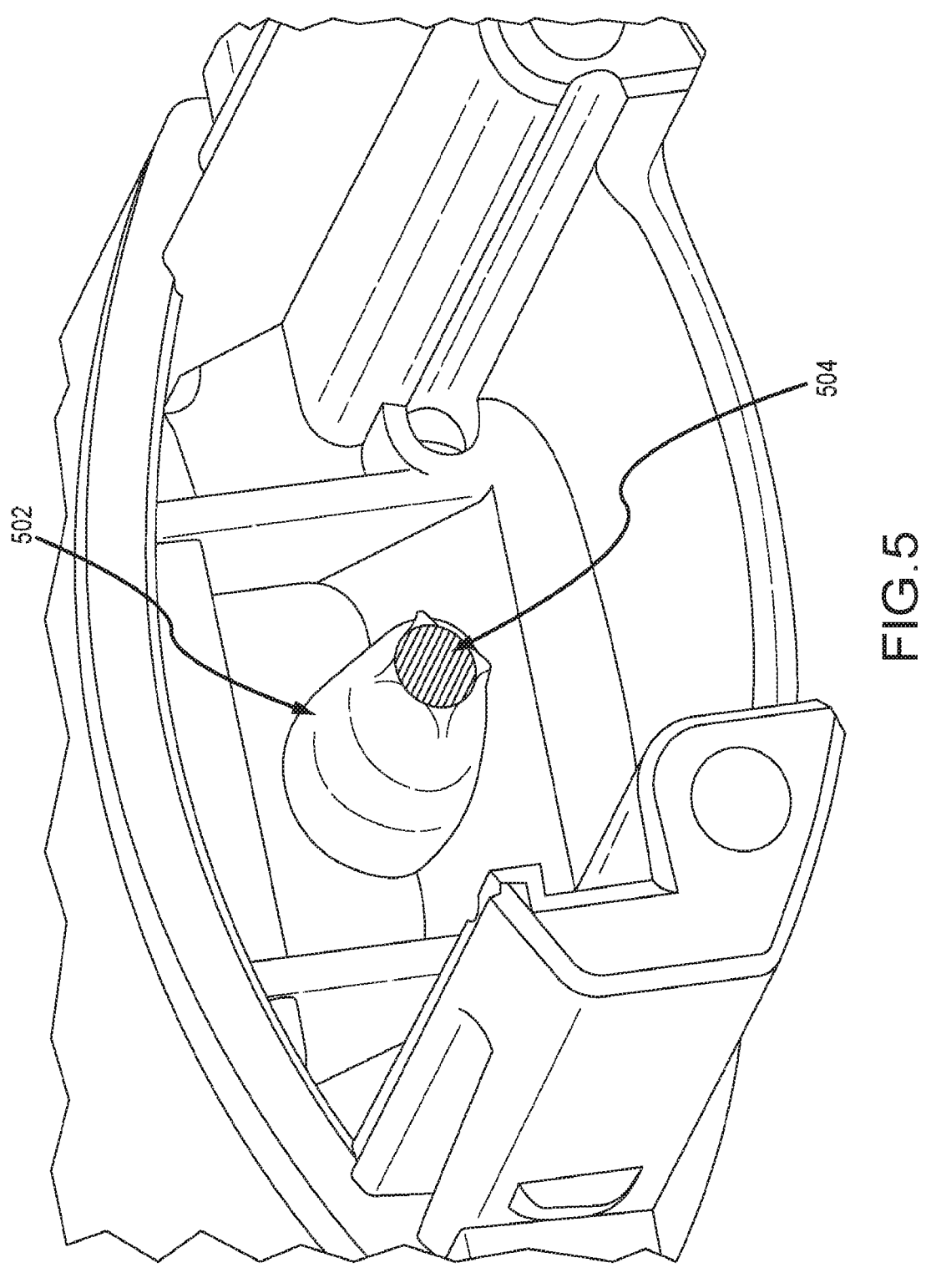
FIG. 5 illustrates a perspective view of a mouthpiece having a fluid transport mating extension, in accordance with one embodiment of the disclosure.
Figure 6A:
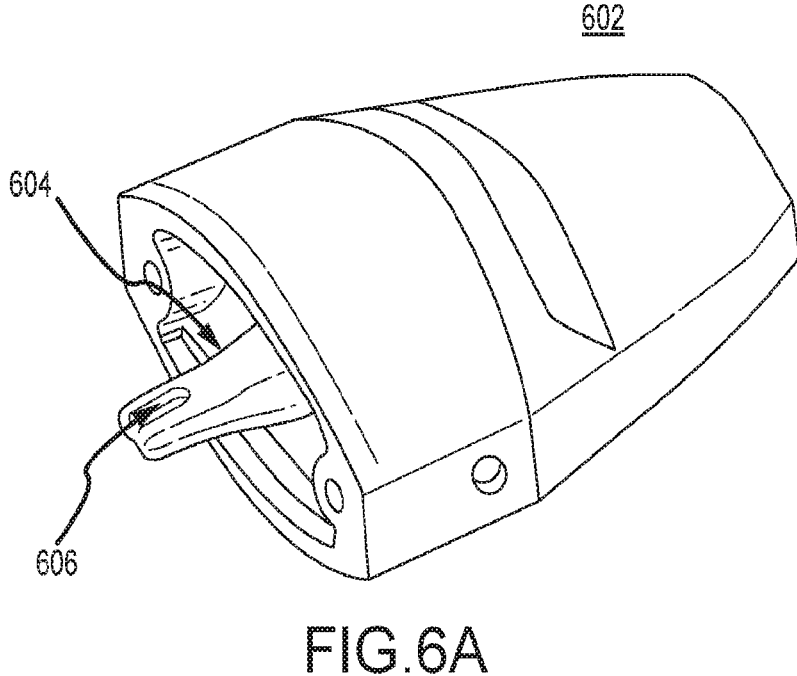
FIG. 6A and FIG. 6B illustrate alternative configurations of a mouthpiece having a fluid transport mating extension, in accordance with embodiments of the disclosure.
Figure 6B:
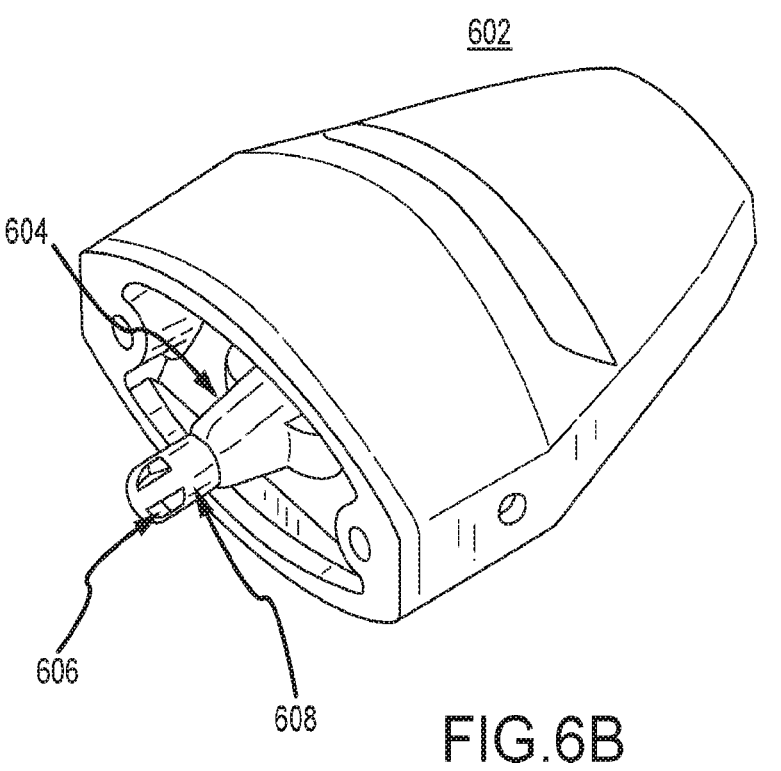

With reference to FIG. 5, in certain embodiments, the mating extension 502 may include one or more capillary fins 504 to direct fluid flow from the fluid cartridge to the ejector mechanism. In certain embodiments, the mating extension may include one or more flow notches. For instance, as illustrated in FIG. 6A, mouthpiece 602 may include mating extension 604, wherein the mating extension 604 includes one or more flow notches 606 on the external surface of the mating extension 604. As illustrated, one flow notch 606 is shown, however, there may be a similar flow notch on the opposite side of the mating extension. In another embodiments, as illustrated in FIG. 6B, the mouthpiece 602 may include mating extension 604, wherein the mating extension 604 includes a cover 608 comprising one or more flow notches 606. Without intending to be limited, the cover 608 may be configured to provide structure integrity to the mating extension 604 while allowing for fluid flow through the notches 606.

Figures 7A, 7B, 7C, 7D, 7E:
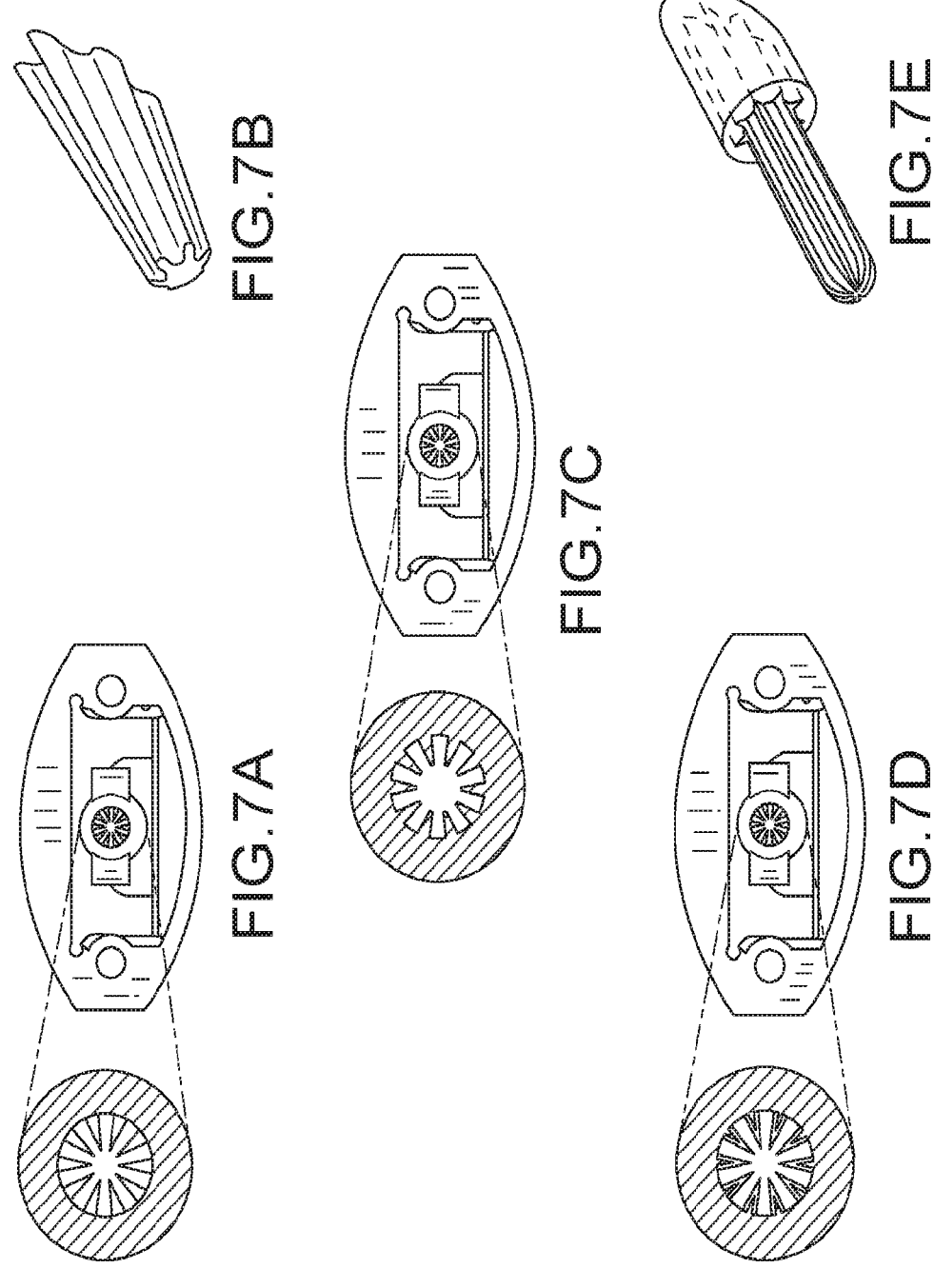
FIGS. 7A-7E illustrate various embodiments of a fluid transport mating extension comprising a capillary flow tube, in accordance with embodiments of the disclosure.

In other embodiments, the mating extension may be configured to include a capillary flow tube. For instance, with reference to FIGS. 7A-7E, the capillary flow tube may be a solid rod with an external capillary structure to provide flow channels (FIG. 7A-7B), a hollow tube with an internal capillary structure to provide flow channels (FIG. 7C), or a combination tube with internal capillary structure and a rod with an external capillary structure to provide flow channels (FIGS. 7D-7E). If desired, the mating extension may be formed from or comprise a wicking material, or may be surface treated to provide a desired surface contact angle. For instance, the mating extension and/or the capillary flow tube may be formed from a metal or polymer and surface treated so as to be hydrophilic, e.g., via micromolding, chemical etching, dry etching (e.g., with ionized oxygen or plasma), etc.

FIGS. 8A-8C illustrate various embodiments of mouthpieces 802 interfaced with fluid cartridges 804, wherein the mouthpiece 802 comprise an exemplary mating extension 806. FIG. 8A illustrates an embodiment wherein the mating extension 806 includes an internal flow channel 810 that may optionally include a wicking material (not shown). FIG.

8B illustrates an embodiment wherein the mating extension 806 includes a capillary flow tube 812 located in a portion of the internal flow channel 810. FIG. 8C illustrates a similar configuration comprising a capillary flow tube 812, however the capillary flow tube 812 is longer so as to extend into the fluid cartridge to a greater extent during use.

Figures 9A, 9B:
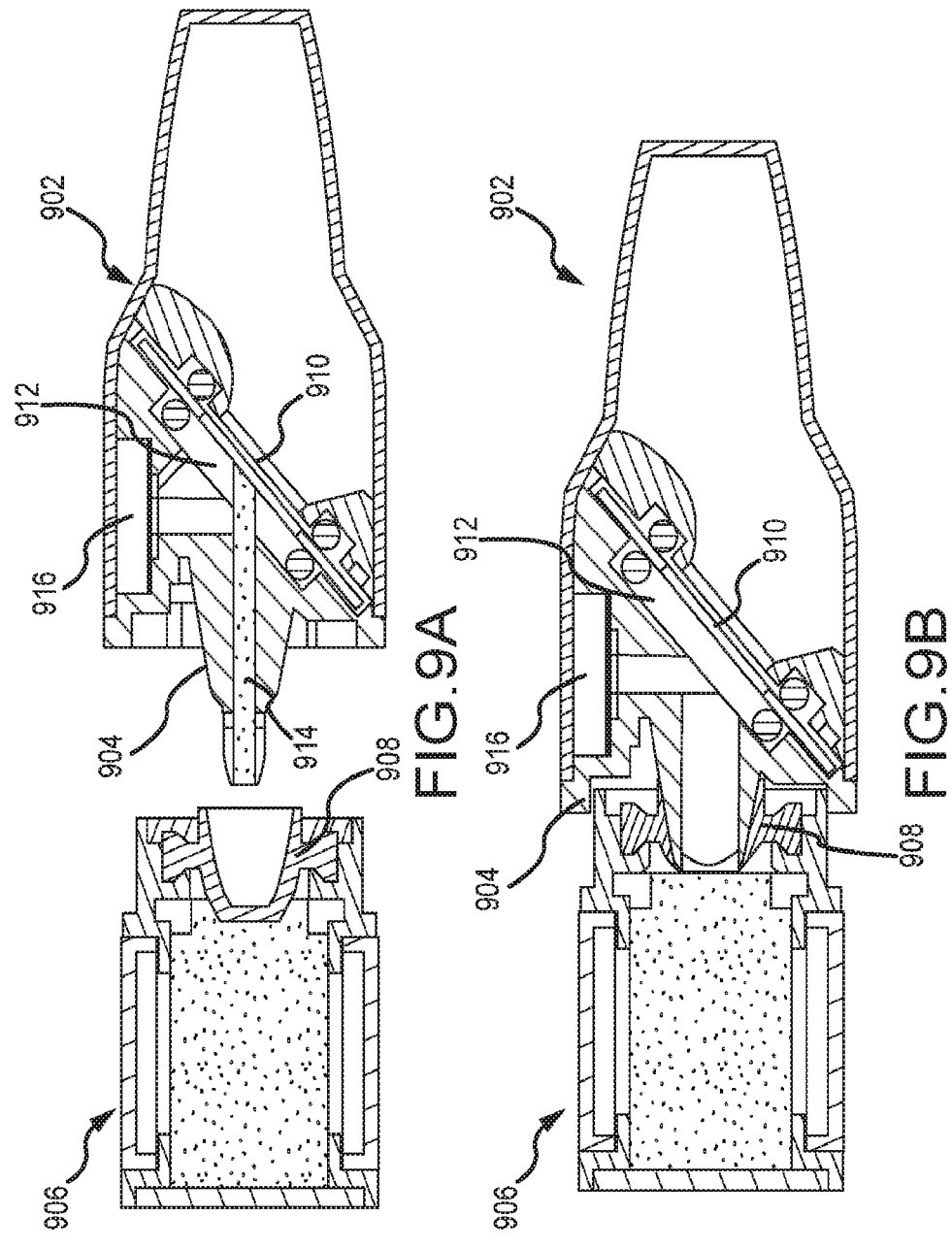
FIGS. 9A-9D illustrate cross-sections of a various configurations of a mouthpiece having a fluid transport mating extension and a fluid cartridge, in accordance with embodiments of the disclosure.
Figures 9C, 9D:
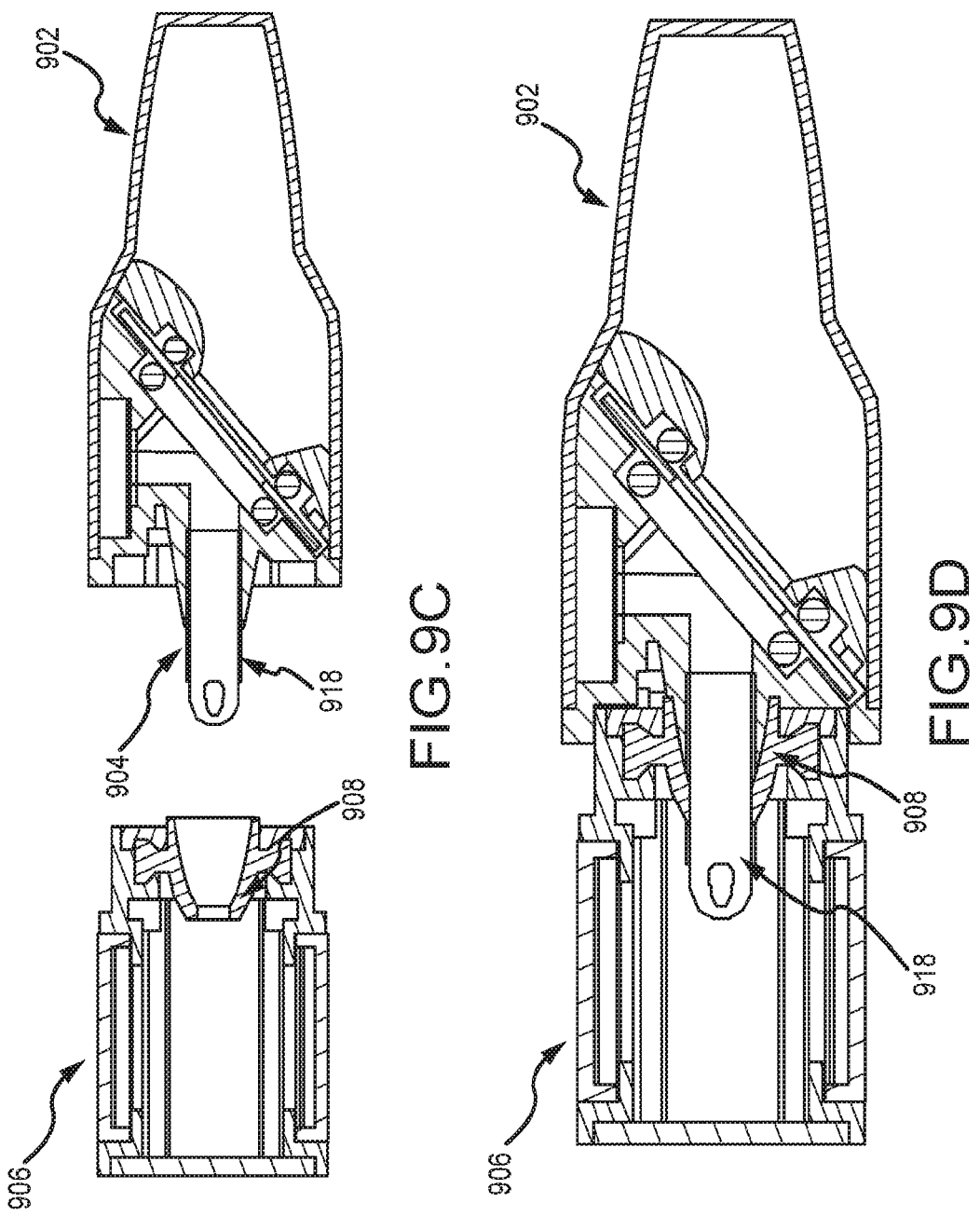

FIGS. 9A-9D illustrate a mouthpiece 902 having a mating extension 904 and a fluid cartridge 906 having a self-sealing stopper 908. FIG. 9A illustrates the mouthpiece 902 and fluid cartridge 906 as separated components, while FIG. 9B illustrates the mouthpiece 902 interfaced with the fluid cartridge 906. The mouthpiece 902 includes an ejector mechanism 910 configured at an angle relative to the direction of air flow, and an ejection chamber 912 on the fluid cartridge facing side of the ejector mechanism 910. The mating extension 904 comprises a wicking material 914 along the internal flow channel to facilitate fluid flow between the fluid cartridge 906 and the ejector mechanism 910 when in use. The mouthpiece may further include one or more vents 916 on the fluid cartridge facing side of the ejector mechanism 910. FIGS. 9C-9D illustrate an alternative configuration of the mating extension 904, wherein the mating extension includes a capillary flow tube 918. FIG. 9C illustrates the mouthpiece 902 and fluid cartridge 906 as separated components, while FIG. 9D illustrates the mouthpiece 902 interfaced with the fluid cartridge 906.

Figures 10A, 10B:
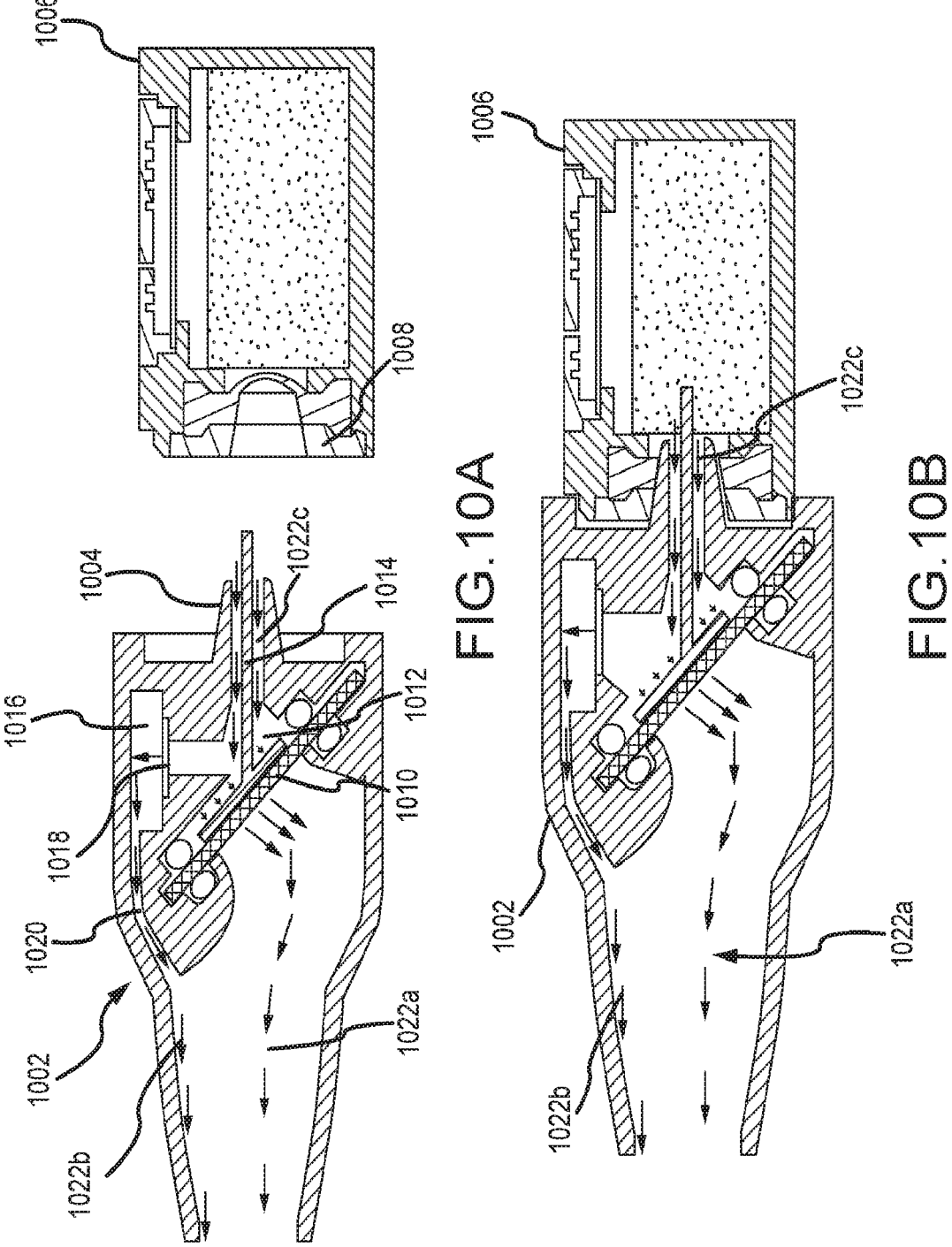
FIGS. 10A-10B illustrate a cross-section of another configuration of a mouthpiece having a fluid transport mating extension and a fluid cartridge, with fluid flow paths exemplified, in accordance with embodiments of the disclosure.

FIGS. 10A-10B illustrate an alternative configuration of a mouthpiece 1002 having a mating extension 1004 and a fluid cartridge 1006 having a self-sealing stopper 1008. FIG. 10A illustrates the mouthpiece 1002 and fluid cartridge 1006 as separated components, while FIG. 10B illustrates the mouthpiece 1002 interfaced with the fluid cartridge 1006. The mouthpiece 1002 includes an ejector mechanism 1010 configured at an angle relative to the direction of air flow, and an ejection chamber 1012 on the fluid cartridge facing side of the ejector mechanism 1010. The mating extension 1004 comprises a wicking material and/or capillary flow tube 1014 along the internal flow channel to facilitate fluid flow between the fluid cartridge 1006 and the ejector mechanism 1010 when in use. The mouthpiece 1002 may further include one or more vents 1016 on the fluid cartridge facing side of the ejector mechanism 1010.

In the embodiment shown, vent 1016 includes an internal super hydrophobic filter or surface treated mesh 1018 on the fluid facing side, and an external opening or flow path 1020 to the air flow exit side of the mouthpiece 1002. In certain embodiments, the internal filter/mesh may be formed from a polymer (e.g., polytetrafluoroethylene (PTFE)) or metal mesh with openings formed therethrough to provide for venting. The mesh may be surface treated so as to have a desired surface contact angle (e.g., so as to be hydrophilic or hydrophobic, depending on its intended use). Generally, if the surface contact angle for water is smaller than 90°, the surface is considered hydrophilic and if the surface contact angle for water is larger than 90°, the surface is considered hydrophobic. In certain embodiments, the mesh may be surface treated to as to achieve a high contact angle (i.e., hydrophobic), or to achieve a low contact angle (i.e., hydrophilic). By way of non-limiting example, the mesh may be surface treated, e.g., via micromolding, chemical etching, dry etching (e.g., with ionized oxygen or plasma), etc.

As shown, when air flow is initiated through the air flow exit side of the mouthpiece 1002 and the droplet deliver device is activated, the stream of droplets is ejected from the ejector mechanism 1010 so as to flow along droplet flow path 1022a. Simultaneously, the fluid cartridge side of the ejector mechanism 1010 may be vented through vent 1016 to create air flow along a suction air flow path 1022b. Without intending to be limited, such a configuration including vent 1016 and suction flow path 1022b can improve ejector mechanism 1010 function by further facilitating wicking fluid flow 1022c from the fluid cartridge 1006 to the ejection chamber 1012 and by facilitating the removal of any air bubbles in the ejection chamber 1012.

As discussed herein, the fluid cartridge may include one or more fluid reservoirs. In certain embodiments, the fluid reservoir may be configured as a container for storing a volume of fluid. In other embodiments, the fluid reservoir may be a sealed container, and may be collapsible or otherwise compressible during use. For instance, with reference to FIGS. 11A-11D, embodiments of a collapsible fluid reservoir are shown. In FIGS. 11A-11B, the fluid reservoir comprises a collapsible bag 1104 that is housed within the fluid cartridge 1102 (FIG. 11A). During use, the mating extension 1106 of a mouthpiece (not shown) is interfaced in fluid communication with the fluid cartridge 1102. As fluid is consumed during use, the collapsible bag 1104 is collapsed within the fluid cartridge 1102 (FIG. 11B). As shown, the collapsible bag 1104 may be secured to the fluid cartridge 1102 at the self-sealing stopper 1108. In other embodiments, as shown in FIGS. 11C-11D, the collapsible bag 1104 may be secured to the fluid cartridge 1102 at a point along the exterior wall of the fluid cartridge, e.g., at a central of mid-way point of the fluid cartridge (FIG. 11C). Again, during use, the mating extension 1104 of a mouthpiece (not shown) is interfaced in fluid communication with the fluid cartridge 1102. As fluid is consumed during use, the collapsible bag 1104 is collapsed within the fluid cartridge 1102 (FIG. 11D). The fluid cartridge 1102 includes one or more vents 1110 to allow the pressure external to the collapsible bag 1104 to equalize.

In certain embodiments, the fluid cartridge may further include fluid displacement elements (e.g., spheres or cylinders) within its volume that are formed from a material or include a material in its composition that has a density greater than that of the fluid to be dispensed. The fluid displacement elements are configured to move, roll, or otherwise be positioned within the fluid reservoir to the lowest point within the reservoir during use, thereby displacing fluid and reducing the dead space volume within the reservoir to improve fluid/aperture plate contact surface area.

In accordance with certain aspects of the disclosure, effective deposition into the lungs generally requires droplets less than about 5-6 μm in diameter, preferably less than about 5 μm, less than about 4 μm, less than about 3 μm, less than about 2.5 μm, less than about 2.3 μm, less than about 2 μm, less than about 1.6 μm, less than about 1.3 μm, less than about 1 μm, etc. Without intending to be limited by theory, to deliver fluid to the lungs a droplet delivery device must impart a momentum that is sufficiently high to permit ejection out of the device, but sufficiently low to prevent deposition on the tongue or in the back of the throat. Droplets below approximately this size are transported almost completely by motion of the airstream and entrained air that carry them and not by their own momentum.

In certain aspects, the present disclosure includes and provides an ejector mechanism configured to eject a stream of droplets within the respirable range of less than about 5-6 μm, preferably less than about 5 μm, less than about 4 microns, less than about 3 microns, less than about 2.5 microns, less than about 2.3 microns, less than about 2 microns, less than about 1.6 microns, less than about 1.3 microns, less than about 1 micron, etc. The ejector mechanism is comprised of a piezo element and optional ultrasonic horn, as described herein. The ejector mechanism is vibrationally coupled to at least one aperture plate, as described herein. The aperture plate generally includes a plurality of openings formed through its thickness and the ejector mechanism oscillates the aperture plate (via its vibrational energy), which has fluid in contact with one surface of the aperture plate, to thereby generate a directed aerosol stream of droplets through the openings of the aperture plate into the lungs as the user inhales.

The ejected stream of droplets includes, without limitation, droplets formed from solutions, suspensions or emulsions which have viscosities in a range capable of droplet formation using the ejector mechanism and aperture plate. In certain aspects, the therapeutic agents may be delivered at a high dose concentration and efficacy, as compared to alternative dosing routes and standard inhalation technologies.

In certain embodiments, the droplet delivery devices of the disclosure may be used to deliver any suitable substance or agent to the respiratory system of a user. For example, the droplet delivery devices may be used to delivery therapeutic agents including small and large molecules. In certain embodiments, the ultrasonic droplet delivery devices of the disclosure may be used to treat various diseases, disorders and conditions by delivering therapeutic agents to the respiratory system of a subject. In this regard, the ultrasonic droplet delivery devices may be used to deliver therapeutic agents both locally to the respiratory system, and systemically to the body.

In certain embodiments, the devices and methods may be used to deliver a composition comprising an agent that may isolated or derived from cannabis. For instance, the agent may be a natural or synthetic cannabinoid, e.g., THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), and various combinations thereof. In other embodiments, the agent may be a ligand that bind the cannabinoid receptor type 1 (CB$_1$), the cannabinoid receptor type 2 (CB$_2$), or combinations thereof. In particular embodiments, the agent may comprise THC, CBD, or combinations thereof. By way of example, the agent may comprise 95% THC, 98% THC, 99% THC, 95% CBD, 98% CBD, 99% CBD, etc.

In other embodiments, the devices and methods of the disclosure may be used to deliver a solution of nicotine or a salt thereof, e.g., including the water-nicotine azeotrope. By way of non-limiting example, the nicotine or salt thereof may be the naturally occurring alkaloid compound having the chemical name S-3-(1-methyl-2-pyrrolidinyl)pyridine, which may be isolated and purified from nature or synthetically produced in any manner, or any of its occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, pyruvate, saccharate, benzoate, methanesulfonate, ethanesulfonate, benzenesulfonate, p-toluene sulfonate, camphorate and pamoate salts. In other embodiments, the composition may further include any pharmacologically acceptable derivative, metabolite or analog of nicotine which exhibits pharmacotherapeutic properties similar to nicotine. Such derivatives and metabolites are known in the art, and include cotinine, norcotinine, nornicotine, nicotine N-oxide, cotinine N-oxide, 3-hydroxycotinine and 5-hydroxycotinine or pharmaceutically acceptable salts thereof.

In certain embodiments, the methods and droplet delivery devices of the disclosure may be used to treat various diseases, disorders and conditions by delivering agents to the respiratory system of a subject. In this regard, the droplet delivery devices may be used to deliver therapeutic agents both locally to the respiratory system, and systemically to the body. In certain embodiments, the methods and droplet delivery devices of the disclosure may be used to treat epilepsy, seizure disorders, pain, chronic pain, neuropathic pain, headache, migraine, arthritis, multiple sclerosis, anorexia, nausea, vomiting, anorexia, loss of appetite, anxiety, insomnia, etc. In other embodiments, the methods and in-line droplet delivery devices of the disclosure may be used to treat asthma and/or COPD.

In certain embodiments, the ultrasonic drug delivery device of the disclosure may be used to deliver scheduled and controlled substances such as narcotics for the highly controlled dispense of pain medications where dosing is monitored or otherwise controlled.

In certain embodiments, by way of non-limiting example, activation and/or droplet delivery may only enabled by a specific user identification by the device or via communication to the device, a doctor or pharmacy communication to the device, only in a specific location (such as the patient's residence, not near a school or other prohibited location, etc., as verified by GPS location on the user's smart phone), and/or it may be controlled by monitoring compliance with administration schedules, amounts, abuse compliances, etc. In certain aspects, this mechanism of highly controlled dispensing of substances can prevent the abuse or overdose of controlled substances.

In other embodiments, the ultrasonic droplet delivery device may be used to deliver therapeutic agents as an ejected stream of droplets to the respiratory system of a subject for the treatment or prevention of respiratory diseases or disorders such as asthma, chronic obstructive respiratory diseases (COPD) cystic fibrosis (CF), tuberculosis, chronic bronchitis, or pneumonia. In certain embodiments, the ultrasonic droplet delivery device may be used to deliver therapeutic agents such as COPD medications, asthma medications, or antibiotics. By way of non-limiting example, such therapeutic agents include albuterol sulfate, ipratropium bromide, tobramycin, fluticasone propionate, fluticasone furoate, tiotropium, glycopyrrolate, olodaterol, salmeterol, umeclidinium, and combinations thereof.

In other embodiments, the ultrasonic droplet delivery device may be used for the systemic delivery of therapeutic agents including small molecules, therapeutic peptides, proteins, antibodies, and other bioengineered molecules via the respiratory system. By way of non-limiting example, the in-line droplet delivery device may be used to systemically deliver therapeutic agents for the treatment or prevention of indications inducing, e.g., diabetes mellitus, rheumatoid arthritis, plaque psoriasis, Crohn's disease, hormone replacement, neutropenia, nausea, influenza, etc.

By way of non-limiting example, therapeutic peptides, proteins, antibodies, and other bioengineered molecules include: growth factors, insulin, vaccines (Prevnor—Pneumonia, Gardasil—HPV), antibodies (Keytruda (pembrolizumab), Opdivo (nivolumab) Avastin (bevacizumab), Humira (adalimumab), Remicade (infliximab), Herceptin (trastuzumab)), Fc Fusion Proteins (Enbrel (etanercept), Orencia (abatacept)), hormones (Elonva—long acting FSH, Growth Hormone), enzymes (Pulmozyme—rHu-DNAase-), other proteins (Clotting factors, Interleukins, Albumin), gene therapy and RNAi, cell therapy (Provenge—Prostate cancer vaccine), antibody drug conjugates—Adcetris (Brentuximab vedotin for HL), cytokines, anti-infective agents, polynucleotides, oligonucleotides (e.g., gene vectors), or any combination thereof; or solid droplets or suspensions such as Flonase (fluticasone propionate) or Advair (fluticasone propionate and salmeterol xinafoate).

As discussed above, effective delivery of droplets deep into the lung airways require droplets that are less than about 5-6 microns in diameter, specifically droplets with mass mean aerodynamic diameters (MMAD) that are less than about 5 microns. The mass mean aerodynamic diameter is defined as the diameter at which 50% of the droplets by mass are larger and 50% are smaller. In certain aspects of the disclosure, in order to deposit in the alveolar airways, droplets in this size range must have momentum that is sufficiently high to permit ejection out of the device, but sufficiently low to overcome deposition onto the tongue (soft palate) or pharynx.

In certain aspects, the droplet delivery device is capable of delivering a defined volume of fluid in the form of an ejected stream of droplets having a small diameter such that an adequate and repeatable high percentage of the droplets are delivered into the desired location within the airways, e.g., the alveolar airways of the subject during use. In certain embodiments, the droplet diameters may range from about 0.7 μm to about 5 μm, about 0.7 μm to about 4.7 μm, about 0.7 μm to about 4 μm, about 0.7 μm to about 2.5 μm, about 0.7 μm to about 1.3 etc.

In other aspects of the disclosure, methods for generating an ejected stream of droplets for delivery to the respiratory system of user using the droplet delivery devices of the disclosure are provided. In certain embodiments, the ejected stream of droplets is generated in a controllable and defined droplet size range. By way of example, the droplet size range includes at least about 50%, at least about 60%, at least about 70%, at least about 85%, at least about 90%, between about 50% and about 90%, between about 60% and about 90%, between about 70% and about 90%, between about 70% and about 95%, etc., of the ejected droplets are in a respirable range of below about 6 preferably below about 5 μm.

In other embodiments, the ejected stream of droplets may have one or more diameters, such that droplets having multiple diameters are generated so as to target multiple regions in the airways (mouth, tongue, throat, upper airways, lower airways, deep lung, etc.) By way of example, droplet diameters may range from about 0.25 μm to about 200 μm, about 0.25 μm to about 100 μm, about 0.25 μm to about 60 μm, about 0.25 μm to about 40 μm, about 0.25 μm to about 20 μm, about 0.25 μm to about 5 μm, about 0.25 μm to about 4.7 μm, about 0.25 μm to about 4 μm, about 6 μm to about 50 μm, about 10 μm to about 10 μm, about 10 μm to about 10 μm to 40 μm, about 10 μm to 30 μm, about 10 μm to 20 μm, about 5 μm to about 10 μm, about 0.7 μm to about 5 μm, about 0.7 μm to about 4.7 μm, about 0.7 μm to about about 0.7 μm to about 2.5 μm, about 0.7 μm to about 1.3 and combinations thereof.

In particular embodiments, at least a fraction of the droplets have diameters in the respirable range, while other droplets may have diameters in other sizes so as to target non-respirable locations (e.g., larger than about 5 μm). Illustrative ejected droplet streams in this regard might have 50%-70% of droplets in the respirable range (less than about 5 μm), and 30%-50% outside of the respirable range, e.g., so as to target the mouth and/or throat (about 5 μm-about 10 μm, about 5 μm-about 20 μm, about 5 μm-about 30 μm, about 10 μm-about 30 etc.)

In certain configurations, a single ultrasonic actuator and single aperture plate may be used to eject a stream of droplets having droplets with more than one diameter. In other embodiments, multiple ultrasonic actuators and multiple aperture plates may be used (together with multiple fluid cartridges or a single fluid cartridge with multiple fluid reservoirs interfaced with multiple aperture plates). In yet other embodiments, a single ultrasonic actuator with multiple aperture plates, again together with multiple fluid cartridges or a single fluid cartridge with multiple fluid reservoirs, may be used.

By way of non-limiting example, a stream of droplets having some droplets with an average droplet diameter of about 0.25 μm to about 5, about 0.7 μm to about 5 μm, about 0.7 μm to about 4.7 μm, about 0.7 μm to about 4 μm, about 0.7 μm to about 2.5 μm, about 0.7 μm to about 1.3 etc., and other droplets having an average droplet diameter of about 10 to 100 μm, about 10 μm to 50 μm, about 10 μm to 40 μm, about 10 μm to 30 μm, about 10 μm to 20 etc., may be ejected. In some embodiments, the smaller droplets may comprise a composition for delivery to the lungs, e.g., nicotine, while the larger droplets may comprise a composition for delivery to the mouth and throat, e.g., a flavorant. In other embodiments, the composition to be delivered via the smaller and larger droplets may be the same. For instance, in some embodiments, the composition may be the same, but may be delivered to the lungs via the smaller droplets at one concentration (dosage), and delivered to the mouth and/or throat via the larger droplets at a second concentration. In some embodiments, the composition may comprise a substance such as nicotine, a cannabinoid, or a medicament.

In certain embodiments, an exemplary device configured to eject more than one stream of droplets having different average droplet diameters may comprise an aperture plate/cartridge configured to interface with a single ultrasonic actuator, the aperture plate/cartridge comprising two fluid reservoirs and two aperture plates having openings of different diameters. The reservoirs and aperture plates are separated by a structural divider element located in the ultrasonic actuator interface zone. In other embodiments, the device may be configured with separate ultrasonic actuator elements interfaced with separate aperture plate/fluid reservoir modules. In yet other embodiments, the device may be configured with a single ultrasonic actuator element interfaced with separate aperture plate/fluid reservoir modules.

Figure 12:
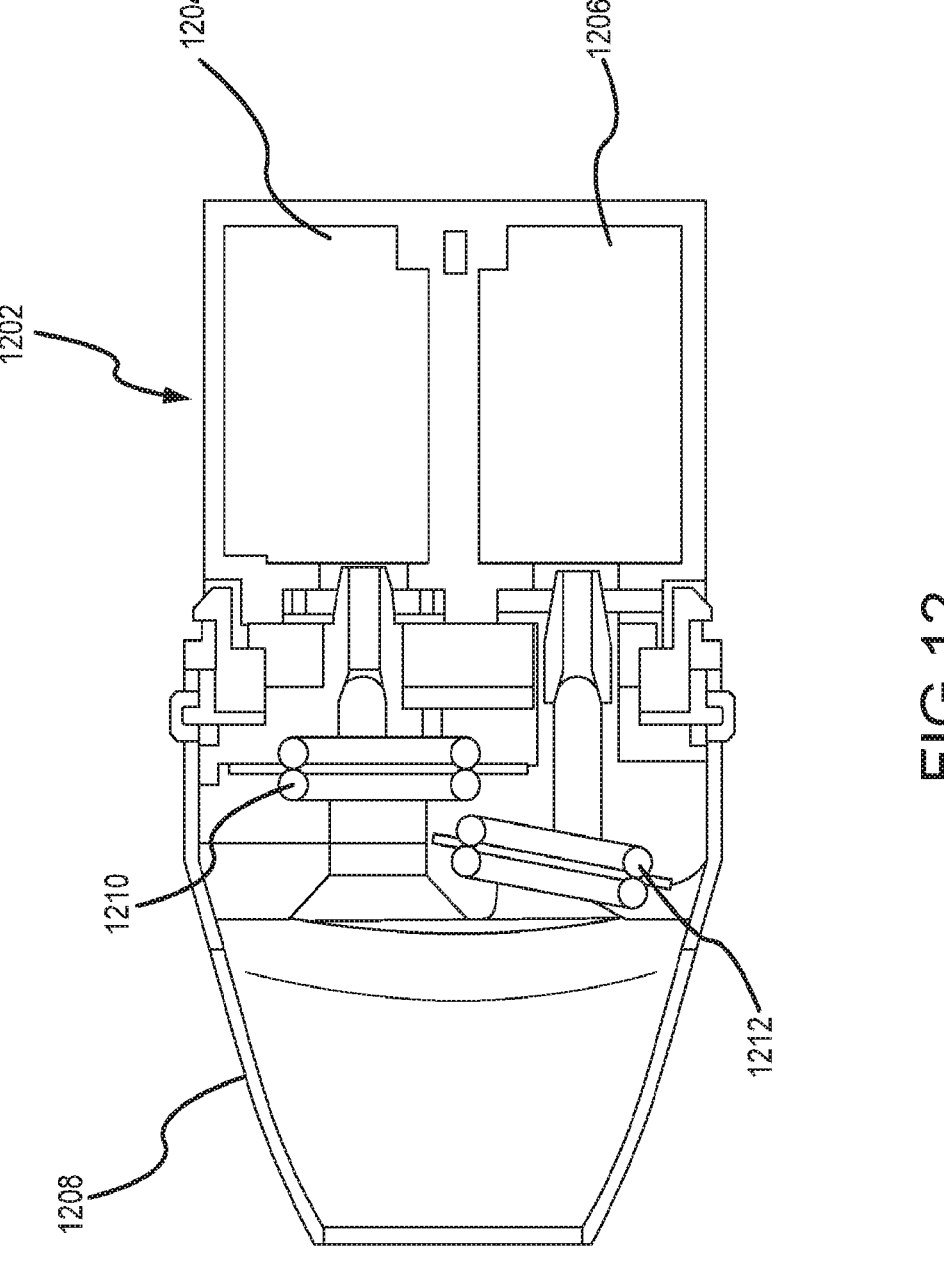
FIG. 12 shows a cross-section of a mouthpiece/fluid cartridge having two ejector mechanisms, and two fluid reservoirs. In the embodiment illustrated, the ejector mechanisms and fluid reservoirs are located generally side-by-side.
Figures 13A, 13B:
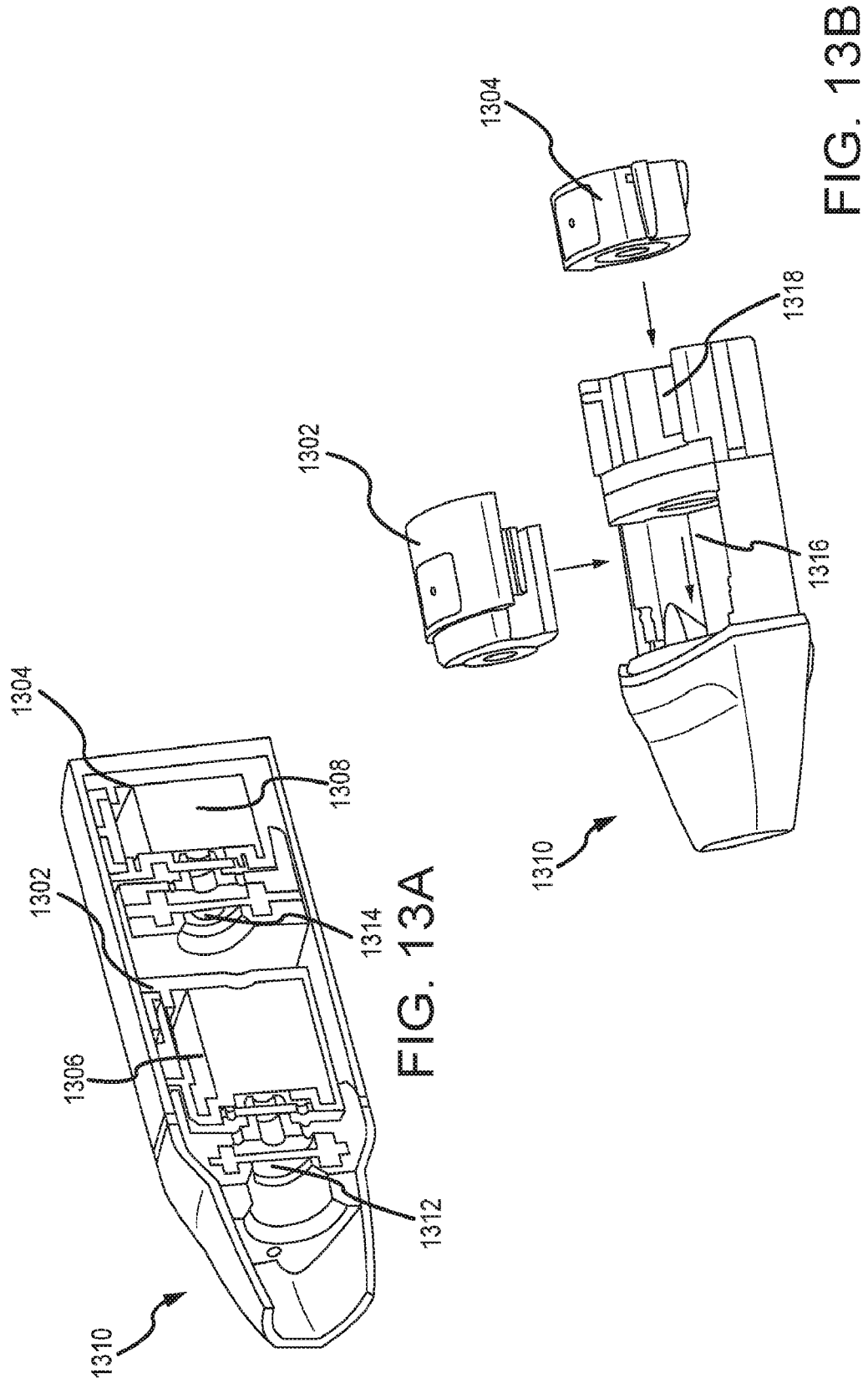
FIG. 13A shows a cross-section of a mouthpiece/fluid cartridge having two ejector mechanisms, and two separate fluid cartridges, each having a fluid reservoir. In the embodiment illustrated, the ejector mechanisms and fluid cartridges are located generally front to back.
FIG. 13B shows a perspective view of the mouthpiece and fluid cartridges of FIG. 13A as separate elements, aligned for insertion of the fluid cartridges into the mouthpiece.

By way of non-limiting example, FIG. 12 and FIGS. 13A-13B illustrate several embodiments that exemplify droplet delivery devices with various combinations of aperture plates, reservoirs, and ultrasonic actuators to facilitate delivery of droplets having more than one diameter.

For instance, with reference to FIG. 12, an embodiment is illustrated wherein the fluid cartridge 1202 comprises two fluid reservoirs 1204, 1206 located side by side. Mouthpiece 1208 includes two ejector mechanisms 1210, 1212, also located generally side by side. In the embodiment illustrated, the ejector mechanisms 1210, 1212 are located offset from one another in a generally side by side configuration. As shown, one of the ejector mechanisms 1210 is oriented generally perpendicularly (vertically), with reference to the direction of air flow through the device. The other ejector mechanism 1212 is oriented at an angle relative to the direction of air flow through the device.

In another embodiment, with reference to FIGS. 13A-13B, the device may include two fluid cartridge 1302, 1304, each comprising a fluid reservoir 1306, 1308, the cartridges located generally front to back. Mouthpiece 1310 includes two ejector mechanisms 1312, 1314, also located generally front to back (FIG. 13A). In the embodiment illustrated, the ejector mechanisms 1312, 1314 are located offset from one another in a generally front to back configuration, and configured to allow air flow from the back ejector mechanism 1314 to the exit side of the mouthpiece 1310. Again, one of the ejector mechanisms may be oriented generally perpendicularly (vertically), with reference to the direction of air flow through the device, and the other may be oriented at an angle relative to the direction of air flow through the device (not shown). In certain embodiments, the individual fluid cartridges 1302, 1304 may be interfaced with the mouthpiece 1310 via separate access points 1316, 1318, again generally located front to back (FIG. 13B).

In another aspect of the disclosure, methods for delivering safe, suitable, and repeatable dosages of a substance, e.g., a medicament, to the respiratory system using the droplet delivery devices of the disclosure are provided. The methods deliver an ejected stream of droplets to the desired location within the respiratory system of the subject, including the deep lungs and alveolar airways.

In certain embodiments, the ultrasonic droplet delivery device is comprised of a separate fluid cartridge including a fluid reservoir and aperture plate, and a handheld base unit (e.g., housing/body) including an ejector mechanism, a differential pressure sensor, a microprocessor and three AAA batteries. In certain embodiments, the handheld base unit also includes a mouthpiece, optionally removable, an optional mouthpiece cover, and an optional ejector plate seal. The microprocessor controls dose delivery, dose counting and software designed monitoring parameters that can be transmitted through blue-tooth technology. The ejector mechanism optimizes droplet delivery to the lungs by creating an ejected droplet stream in cooperation with the aperture plate in a predefined range with a high degree of accuracy and repeatability. Initial droplet studies show at least 65% to 70% of droplets ejected from the device are in the respirable range (e.g., 1-5 μm).

In certain embodiments, the ultrasonic droplet delivery device may include a fluid cartridge including one or more fluid reservoirs, which fluid cartridge may be replaceable or disposable either on a periodic basis, e.g., a daily, weekly, monthly, as-needed, etc. basis. The fluid reservoir may be prefilled and stored in a store or pharmacy for dispensing to users, or filled at the store, pharmacy or elsewhere by using a suitable injection means such as a hollow injection syringe driven manually or driven by a micro-pump. The syringe may fill the reservoir by pumping fluid into or out of a rigid container or other collapsible or non-collapsible reservoir. In certain aspects, such a fluid cartridge may minimize and prevent buildup of surface deposits or surface microbial contamination on the aperture plate, owing to its short in-use time.

In certain aspects of the disclosure, the mouthpiece and ejector mechanism, and the fluid cartridge function to generate a plume with droplet diameters less than about 5 μm.

As discussed above, in certain embodiments, the ejector mechanism is powered by electronics in the body housing, and the fluid reservoir may carry sufficient substance for a single dose, a few doses, or several hundred doses of medicament.

In certain aspects, the devices of the disclosure eliminate the need for user/device coordination by using a differential pressure sensor to initiate the piezoelectric ejector in response to the onset of inhalation.

As described herein, in certain embodiments, the ultrasonic droplet delivery device may be turned on and activated for use by inserting the mouthpiece/fluid cartridge into the body housing, opening the mouthpiece cover (if present), and/or switching an on/off switch, slide bar, or button. In certain embodiments, visual and/or audio indicators may be used to indicate the status of the device in this regard, e.g., on, off, stand-by, preparing, etc. By way of example, one or more LED lights may turn green and/or flash green to indicate the device is ready for use. In other embodiments, visual and/or audio indicators may be used to indicate the status of the fluid cartridge, including the number of inhalations taken, the number of inhalations remaining, instructions for use, etc. For example, and LED visual screen may indicate an inhalation counter numerical display with the number of remaining inhalations in the reservoir.

As described in further detail herein, during use as a user inhales through the mouthpiece of the ultrasonic droplet delivery device of the disclosure, a differential pressure sensor within the device detects inspiratory flow, e.g., by measuring the pressure drop across a Venturi plate or other suitable pressure sensor, e.g., located within the mouthpiece or within the body housing. When a threshold pressure decline (e.g., 8 slm) is attained, the microprocessor activates the ejector mechanism, which in turn generates an ejected stream of droplets into the airflow of the device that the user inhales through the mouthpiece. In certain embodiments, audio and/or visual indicates may be used to indicate that dosing has been initiated, e.g., one or more LEDs may illuminate green. The microprocessor then deactivates the ejector at a designated time after initiation so as to achieve a desired administration dosage, e.g., 1-1.45 seconds. Alternatively, the microprocessor may deactivate when the pressure sensor indicates that inhalation is no longer detected. In such embodiments, thresholds may be set to ensure that overdose and abuse does not occur. In certain embodiments, as described in further detail herein, the device may provide visual and/or audio indicators to facilitate proper dosing, e.g., the device may emit a positive chime sound after the initiation of dosing, indicating to the user to begin holding their breath for a designated period of time, e.g., 10 seconds. During the breath hold period, e.g., the three green LEDs may blink. Additionally, there may be voice commands instructing the patient on proper times to exhale, inhale and hold their breath, with an audio indicator of a breath hold countdown.

Following dosing, the ultrasonic droplet delivery device may turned off and deactivated in any suitable manner, e.g., by closing the mouthpiece cover, switching an on/off switch, slide bar, or button, timing out from non-use, removing the fluid cartridge, etc. If desired, audio and/or visual indicators may prompt a user to deactivate the device, e.g., by flashing one or more red LED lights, providing voice commands to close the mouthpiece cover, etc.

In certain embodiments, the ultrasonic droplet delivery device may include an ejector mechanism closure system that seals the aperture plate when not in use to protect the integrity of the aperture plate and to minimize and prevent contamination and evaporation of the fluid within the reservoir. For example, in some embodiments, the device may include a mouthpiece cover that comprises a rubber plug that is sized and shaped to seal the exit side surface of the aperture plate when the cover is closed. In other embodiments, the mouthpiece cover may trigger a slide to seal the exit side surface of the aperture plate when the cover is closed. Other embodiments and configurations are also envisioned, e.g., manual slides, covers, and plugs, etc. In certain aspects, the microprocessor may be configured to detect when the ejector mechanism closure, aperture plate seal, etc. is in place, and may thereafter deactivate the device.

Several features of the device allow precise dosing of specific droplet sizes. Droplet size is set by the diameter of the holes in the aperture plate which are formed with high accuracy. By way of example, the exit side holes in the aperture plate may range in size from 1 μm to 6 μm, from 2 μm to 5 μm, from 3 μm to 5 μm, from 3 μm to 4 μm, etc. In other embodiments, as described herein, if multiple sizes of droplets are desired, the aperture plate may be configured with areas of holes having multiple diameters. For example, the aperture plate may have concentric rings having hole diameters of differing sizes, an internal area having a first hole size diameter, and an external ring having a different hole size diameter, one side having a first size hole diameter and the other side having a second size hole diameter, etc. Ejection rate, in droplets per second, is generally fixed by the frequency of the aperture plate vibration, e.g., 108-kHz, which is actuated by the microprocessor. In certain embodiments, there is less than a 50-millisecond lag between the detection of the start of inhalation and full droplet generation.

Other aspects of the device of the disclosure that allow for precise dosing of specific droplet sizes include the production of droplets within the respirable range early in the inhalation cycle, thereby minimizing the amount of drug product being deposited in the mouth or upper airways at the end of an inhalation. In addition, the design of the fluid cartridge allows the aperture plate surface to be wetted and ready for ejection without user intervention, thus obviating the need for shaking and priming. Further, the design of the fluid cartridge together with the face seal limits fluid evaporation from the reservoir to less than 150 μL to 350 μL per month.

The device may be constructed with materials currently used in FDA cleared devices. Standard manufacturing methods may be employed to minimize extractables.

Any suitable material may be used to form the mouthpiece, fluid cartridge, and body housing of the droplet delivery device. In particular embodiment, the material should be selected such that it does not interact with the components of the device or the fluid to be ejected (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc.

The aperture plate may be metallic or polymer with openings about the diameter of the desired droplets (as discussed further herein). By way of non-limiting example, the aperture plate may formed from silicon, silicon carbide, nickel palladium, or a high stiffness polymer such as polyether ether ketone (PEEK), poly-amide, Kapton or Ultra High Molecular Weight Polyethylene (UHMWPE). In other embodiments, aperture plates may be formed from silicon or silicon carbide. Without being limited, both of these materials can be formed by bulk micro-machining processes such as wet etching.

The aperture plate may have an array of opening ranging from, e.g., 100 to 10,000 openings, 500 to 10,000 openings, etc. The openings may generally have a diameter similar to that of the desired droplets, as described further herein.

Several features of the device allow precise dosing of specific droplet sizes. Droplet size is set by the diameter of the holes in the aperture plate which are formed with high accuracy. By way of example, the exit side holes in the aperture plate may range in size from 1 μm to 100 μm, 1 μm to 50 μm, 1 μm to 20 μm, 1 μm to 6 μm, 2 μm to 5 μm, 3 μm to 5 μm, 3 μm to 4 μm, 5 μm to 50 μm, etc. In other embodiments, as described herein, if multiple sizes of droplets are desired, the aperture plate may be configured with areas of holes having multiple diameters. For example, the aperture plate may have concentric rings having hole diameters of differing sizes, an internal area having a first hole size diameter, and an external ring having a different hole size diameter, one side having a first size hole diameter and the other side having a second size hole diameter, etc. Ejection rate, in droplets per second, is generally fixed by the frequency of the aperture plate vibration, e.g., 108-kHz, which is actuated by the microprocessor. In certain embodiments, there is less than a 50-millisecond lag between the detection of the start of inhalation and full droplet generation.

When using a polymer aperture plate, the holes may be produced by rolling, stamping, laser ablation, bulk etching or other known micro-machining processes. When using silicon and SiC aperture plates, the openings may be formed using typical semiconductor processes. In addition, the aperture plate area can be formed to have a dome-like shape to increase the stiffness of the aperture plate and creating uniform ejection accelerations.

As discussed herein, in certain aspects, the ultrasonic droplet delivery device may include an ejector mechanism having a aperture plate wherein the surface is configured to facilitate generation of droplets with the desired droplet size distribution, e.g., less than 4 μm, less than about 3 microns, less than about 2 microns, less than about 1.5 microns, less than about 1 microns, etc.

In certain embodiments, to facilitate generation of droplets with the desired droplet size distribution, the surface of the aperture plate may be configured (e.g., treated, coated, surface modified, or a combination thereof) to provide a desired surface contact angle at the fluid intake surface of less than about 50 degrees, less than about 40 degrees, less than about 35 degrees, less than about 30 degrees, less than about 20 degrees, less than about 10 degrees, between about 10 and about 35 degrees, between about 15 and about 35 degrees, etc.

In certain embodiments, the aperture plate may be treated or coated on at least the fluid intake side of the aperture plate to achieve a desired hydrophilic surface contact angle. In other embodiments, the aperture plate may be treated or coated on at least a portion of the interior surface of one or more openings, within the entire interior surface of one or more openings, on both the fluid intake surface and the fluid ejection surface of the aperture plate, and combinations thereof.

Without intending to be limited by theory, a hydrophilic surface contact angle is believed to more effectively attract an aqueous composition into the openings of the ejector aperture plate during the vibration of the aperture plate by the piezo element, thereby increasing the mass flow of aerosol droplets out of the aperture plate. A surface is considered to be hydrophilic when that angle is less than about 50 degrees, and considered to be super hydrophilic when that angle is less than about 10 to 20 degrees (droplet tends to spread out across the surface).

In accordance with aspects of the disclosure, exemplary methods for creating a hydrophilic surface on the fluid side of a metallic aperture plate including surface etching methods, dip coating methods and chemical deposition methods. Dip coating methods comprise dipping the metal ejector aperture plate into a solution comprising a desired coating and a solvent, which solution will form a hydrophilic coating on the metal when the solvent evaporates. Chemical depositions methods include known deposition methods, e.g., plasma etch, plasma coating, plasma deposition, CVD, electroless plating, electroplating, etc., wherein the chemical deposition uses a plasma or vapor to open the bonds on the surface of the metal so that oxygen or hydroxyl molecules attach to the surface rendering it polar. In certain embodiments, the deposited hydrophilic layer is significantly thinner than the opening size such that it does not impact the size of the generated droplets.

The fluid cartridge and fluid reservoir may be constructed of any suitable materials for the intended pharmaceutical use. In particular, the composition contacting portions may be made from material compatible with the desired agent(s), e.g., nicotine, albuterol sulfate and ipratropium bromide. By way of example, in certain embodiments, the agent only contacts the inner side of the drug reservoir and the inner face of the aperture plate. In certain embodiments, the fluid reservoir may be configured to hold a single dose or multiple doses of agent. By way of example, the fluid reservoir may hold between 10 to 2000 µL of fluid.

In certain embodiments, the device mouthpiece may be removable, replaceable and may be cleaned. Similarly, the body housing and fluid cartridge can be cleaned by wiping with a moist cloth. In certain embodiments, the mouthpiece may be interfaced with (and optionally removable and/or replaceable), integrated into, or part of the housing. In other embodiments, the mouthpiece may be interfaced with (and optionally removable and/or replaceable), integrated into, or part of the fluid cartridge. In some embodiments, the mouthpiece may be interfaced with (and optionally removable and/or replaceable), integrated into, or part of the body housing and the fluid cartridge.

Again, any suitable material may be used to form the mouthpiece of the droplet delivery device. In particular embodiment, the material should be selected such that it does not negatively interact with the components of the device or the fluid to be ejected (e.g., agent, drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc. In certain embodiments, the mouthpiece may be removable, replaceable and sterilizable. In one embodiment, the mouthpiece tube may be formed from sterilizable and transparent polymer compositions such as polycarbonate, polyethylene or polypropylene, as discussed herein.

In certain aspects of the disclosure, a hydrophobic treatment/coating and/or electrostatic treatment/coating may be applied to the one or more portions of the device, e.g., inner surfaces of the device along the air flow pathway such as the interior surfaces of the mouthpiece, to aid in reducing deposition of ejected droplets during use. In some embodiments, the hydrophobic treatment/coating can minimize droplet deposition due to hydrophobic interactions with the ejected fluid. In other embodiments, the electrostatic treatment/coating can minimize droplet deposition due to electrostatic charge build-up. Alternatively, one or more portions of the mouthpiece, fluid cartridge, or housing may be formed from a charge-dissipative polymer. For instance, conductive fillers are commercially available and may be compounded into the more common polymers used in medical applications, for example, PEEK, polycarbonate, polyolefins (polypropylene or polyethylene), or styrenes such as polystyrene or acrylic-butadiene-styrene (ABS) copolymers. Alternatively, in certain embodiments, one or more portions of the device, e.g., inner surfaces of the device along the airflow pathway such as the mouthpiece, may be coated with anti-microbial coatings, or may be coated with hydrophobic coatings to aid in reducing deposition of ejected droplets during use. Any suitable coatings known for such purposes may be used, e.g., polytetrafluoroethylene (Teflon).

Any suitable differential pressure sensor with adequate sensitivity to measure pressure changes obtained during standard inhalation cycles may be used, e.g., ±5 SLM, 10 SLM, 20 SLM, etc. For instance, pressure sensors from Sensirion, Inc., SDP31 or SDP32 (U.S. Pat. No. 7,490,511 B2) are particularly well suited for these applications.

In certain aspects, the microprocessor in the device may be programmed to ensure exact timing and actuation of the ejector mechanism in accordance with desired parameters, e.g., based duration of piezoelectric activation to achieve desired dosages, etc. In certain embodiments, the device includes or interfaces with a memory (on the device, smartphone, App, computer, etc.) to record the date-time of each ejection event, as well as the user's inhalation flow rate during the dose inhalation to facilitate user monitoring, as well as drug ampoule usage monitoring. For instance, the microprocessor and memory can monitor doses administered and doses remaining in a particular drug ampoule. In certain embodiments, the drug ampoule may comprise components that include identifiable information, and the base unit may comprise components that may "read" the identifiable information to sense when a drug ampoule has been inserted into the base unit, e.g., based on a unique electrical resistance of each individual ampoule, an RFID chip, or other readable microchip (e.g., cryptoauthentication microchip). Dose counting and lockouts may also be preprogramed into the microprocessor.

In certain embodiments of the present disclosure, the signal generated by the pressure sensors provides a trigger for activation and actuation of the ejector mechanism to thereby generate droplets and delivery droplets at or during a peak period of a patient's inhalation (inspiratory) cycle and assures optimum deposition of the plume of droplets and delivery of the medication into the respiratory airways of the user.

In accordance with certain aspects of the disclosure, the ultrasonic droplet delivery device provides a reliable monitoring system that can date and time stamp actual delivery of substance, and record/store inspiratory airflow in a memory (on the device, smartphone, App, computer, etc.). Blue tooth or other wireless communication capabilities may then permit the wireless transmission of the data.

Bluetooth communication in the device will communicate date, time and number of actuations per session to the user's smartphone. Software programing can provide charts, graphics, medication reminders and warnings to patients and whoever is granted permission to the data. The software application will be able to incorporate multiple uses and users of the device (e.g. multiple substances, different users, etc.).

The device of the present disclosure is configured to dispense droplets during the correct part of the inhalation cycle, and can including instruction and/or coaching features to assist patients with proper device use, e.g., by instructing the holding of breath for the correct amount of time after inhalation. The device of the disclosure allows this dual functionality because it may both monitor air flow during the inhalation, and has internal sensors/controls which may detect the end of inhalation (based upon measured flow rate) and can cue the patient to hold their breath for a fixed duration after the inhalation ceases.

In one exemplary embodiment, a patient may be coached to hold their breath with an LED that is turned on at the end of inhalation and turned off after a defined period of time (i.e., desired time period of breath hold), e.g., 10 seconds. Alternatively, the LED may blink after inhalation, and continue blinking until the breath holding period has ended. In this case, the processing in the device detects the end of inhalation, turns on the LED (or causes blinking of the LED, etc.), waits the defined period of time, and then turns off the LED. Similarly, the device can emit audio indications, e.g., one or more bursts of sound (e.g., a 50 millisecond pulse of 1000 Hz), verbal instructions to hold breath, verbal countdown, music, tune, melody, etc., at the end of inhalation to cue a patient to hold their breath for the during of the sound signals. If desired, the device may also vibrate during or upon conclusion of the breath holding period.

In certain embodiments, the device provides a combination of audio and visual methods (or sound, light and vibration) described above to communicate to the user when the breath holding period has begun and when it has ended. Or during the breath holding to show progress (e.g., a visual or audio countdown).

In other aspects, the device of the disclosure may provide coaching to inhale longer, more deeply, etc. The average peak inspiratory flow during inhalation (or dosing) can be utilized to provide coaching. For example, a patient may hear a breath deeper command until they reach 90% of their average peak inspiratory flow as measured during inspiration (dosing) as stored on the device, phone or in the cloud.

In addition, an image capture device, including cameras, scanners, or other sensors without limitation, e.g. charge coupled device (CCD), may be provided to detect and measure the ejected aerosol plume. These detectors, LED, delta P transducer, CCD device, all provide controlling signals to a microprocessor or controller in the device used for monitoring, sensing, measuring and controlling the ejection of a plume of droplets and reporting patient compliance, treatment times, dosage, and patient usage history, etc., via Bluetooth, for example.

In certain embodiments, the ejector mechanism and/or fluid cartridge may include components that may carry information read by the device electronics including key parameters such as ejector mechanism functionality, drug identification, and information pertaining to patient dosing intervals. Some information may be added at the factory, and some may be added at the store or pharmacy. In certain embodiments, information placed by the factory may be protected from modification by the store or pharmacy. The information may be carried as a printed barcode or physical barcode encoded into the device geometry (such as light transmitting holes on a flange which are read by sensors within the device). Information may also be carried by a programmable or non-programmable microchip within the fluid cartridge and/or mouthpiece which communicates to the electronics in the body housing.

By way of example, programming at the factory, store, or pharmacy may include a substance code which may be read by the device, communicated via Bluetooth to an associated user smartphone and then verified as correct for the user. In the event a user inserts an incorrect, generic, damaged, etc., fluid cartridge into the device, the smartphone might be prompted to lock out operation of the device, thus providing a measure of user safety and security not possible with passive inhaler devices. In other embodiments, the device electronics can restrict use to a limited time period (perhaps a day, or weeks or months) to avoid issues related to substance aging or build-up of contamination or particulates within the device.

The ultrasonic droplet delivery device may further include various sensors and detectors to facilitate device activation, spray verification, patient compliance, diagnostic mechanisms, or as part of a larger network for data storage, big data analytics and for interacting and interconnected devices used for subject care and treatment, as described further herein. Further, the body housing may include an LED assembly on a surface thereof to indicate various status notifications, e.g., ON/READY, ERROR, etc.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed:

1. A droplet delivery device comprising:
    a mouthpiece positioned at an airflow exit of the device, the mouthpiece comprising one or more air flow entrance ports, an airflow exit opening, an electronically actuated ejector, an ejection chamber, and a fluid transport mating extension;
    a fluid cartridge including a volume of fluid and at least one self-sealing stopper, the fluid cartridge disposed within or in fluid communication with the mouthpiece;
    a body housing comprising a power source and control board; and
    at least one pressure sensor positioned within the mouthpiece or positioned within the housing and in fluid communication with the mouthpiece, the at least one pressure sensor operably coupled to the ejector to generate an ejected stream of droplets upon sensing a pre-determined pressure change within the mouthpiece;
    wherein the electronically actuated ejector is in fluid communication with the volume of fluid at a fluid cartridge side of the ejector, the ejector comprising a piezoelectric actuator and an aperture plate, the aperture plate having a plurality of openings formed through its thickness and the piezoelectric actuator operable to oscillate the aperture plate at a frequency to thereby generate the ejected stream of droplets;
    wherein the ejection chamber is located adjacent the ejector on the fluid cartridge side of the ejector;
    wherein the fluid transport mating extension interfaces with or extends through the self-sealing stopper to create fluid communication between the fluid cartridge and the ejector;
    wherein the fluid transport mating extension comprises a wicking element extending through the self-sealing stopper into the volume of fluid and configured to draw liquid from the fluid cartridge toward the ejector by capillary action;

wherein the mouthpiece further comprises at least one vent opening positioned on a fluid side of the aperture plate adjacent the ejector; and wherein the at least one vent opening is configured to release air displaced by liquid transported by the wicking element to the ejector to reduce air bubble accumulation at the ejector and maintain substantially continuous droplet generation.

2. The droplet delivery device of claim 1, wherein at least about 50% of the droplets of the ejected stream of droplets have an average ejected droplet diameter of less than about 6 microns, such that at least about 50% of the mass of the ejected stream of droplets is delivered in a respirable range to the pulmonary system of a subject during use.

3. The droplet delivery device of claim 1, wherein the one or more air flow entrance ports of the mouthpiece provide an air inlet flow element, and wherein the air inlet flow element and mouthpiece facilitate non-turbulent airflow across an exit side of the aperture plate and provide airflow through the mouthpiece during use.

4. The droplet delivery device of claim 1, wherein the at least one vent opening includes a vent filter.

5. The droplet delivery device of claim 1, wherein the mouthpiece and ejector are oriented such that the exit side of the aperture plate is perpendicular to the direction of air flow and the stream of droplets is ejected in parallel to the direction of air flow.

6. The droplet delivery device of claim 1, wherein the mouthpiece and ejector are oriented such that the exit side of the aperture plate is oriented at an angle relative to the direction of air flow and the stream of droplets is ejected at an angle to the direction of air flow.

7. The droplet delivery device of claim 1, wherein the mouthpiece is removably coupled to the fluid cartridge.

8. The droplet delivery device of claim 1, wherein at least one of the mouthpiece and fluid cartridge is removably coupled with the body housing.

9. The droplet delivery device of claim 1, wherein the fluid cartridge is coupled to the mouthpiece and forms a module that is removably coupled with the housing.

10. The droplet delivery device of claim 1, wherein one or more of the plurality of openings of the aperture plate have different cross-sectional shapes or diameters.

11. The droplet delivery device of claim 1, wherein the aperture plate is composed of a material selected from the group consisting of poly ether ether ketone (PEEK), polyimide, polyetherimide, polyvinylidine fluoride (PVDF), ultra-high molecular weight polyethylene (UHMWPE), nickel, nickel-cobalt, nickel-palladium, palladium, platinum, metal alloys thereof, and combinations thereof.

12. The droplet delivery device of claim 1, further comprising a wireless communication module.

13. The droplet delivery device of claim 1, further comprising one or more sensors selected from the group consisting of an infra-red transmitter, a photodetector, an additional pressure sensor, and combinations thereof.

14. The droplet delivery device of claim 1, wherein the self-sealing stopper includes one or more cut openings.

15. The droplet delivery device of claim 1, wherein the self-sealing stopper comprises a polymer.

16. The droplet delivery device of claim 15, wherein the fluid transport mating extension comprises a polymer.

17. The droplet delivery device of claim 15, wherein the self-sealing stopper includes one or more cut openings.

18. A method for delivering an agent as an ejected stream of droplets in a respirable range to a pulmonary system of a user, the method comprising:

(a) generating an ejected stream of droplets via the droplet delivery device of claim 1, wherein at least about 50% of the ejected stream of droplets have an average ejected droplet diameter of less than about 6 μm; and (b) delivering the ejected stream of droplets to the pulmonary system of the user such that at least about 50% of the mass of the ejected stream of droplets is delivered in a respirable range to the pulmonary system of the user during use.

19. The method of claim 18, wherein the ejected stream of droplets is delivered over a period of time less than about 2 seconds.

* * * * *